United States Patent [19]

Cimino et al.

[11] Patent Number: 5,532,146

[45] Date of Patent: Jul. 2, 1996

[54] METHOD FOR RENDERING LIGASE-BASED AMPLIFICATION PRODUCTS UNAMPLIFIABLE

[75] Inventors: George D. Cimino, Richmond; Stephen T. Isaacs, Orinda; John W. Tessman, San Francisco, all of Calif.

[73] Assignee: HRI Research, Inc., Concord, Calif.

[21] Appl. No.: 263,020

[22] Filed: Jun. 20, 1994

Related U.S. Application Data

[63] Continuation of Ser. No. 729,972, Jul. 15, 1991, abandoned, which is a continuation-in-part of Ser. No. 428,494, Oct. 26, 1989, Pat. No. 5,221,608.

[51] Int. Cl.$^6$ .............................. C12P 19/34; C07H 21/00
[52] U.S. Cl. .......................... 435/91.2; 435/6; 435/91.1; 435/810; 536/22.1; 536/23.1; 536/25.3; 935/77; 935/78; 935/88
[58] Field of Search .......................... 435/6, 91.1, 91.2, 435/810; 536/22.1, 23.1, 25.3; 935/77, 78, 88

[56] References Cited

U.S. PATENT DOCUMENTS

| | | | |
|---|---|---|---|
| 4,124,598 | 11/1978 | Hearst et al. | 260/343.21 |
| 4,169,204 | 9/1979 | Hearst et al. | 546/270 |
| 4,196,281 | 4/1980 | Hearst et al. | 536/28 |
| 4,599,303 | 7/1986 | Yabusaki et al. | 435/6 |
| 4,683,195 | 7/1987 | Mullis et al. | 435/6 |
| 4,683,202 | 7/1987 | Mullis | 435/91 |
| 5,035,996 | 7/1991 | Hartley | 435/6 |
| 5,139,940 | 8/1992 | Isaacs et al. | 435/91 |
| 5,184,020 | 2/1993 | Hearst et al. | 250/455.11 |
| 5,221,608 | 6/1993 | Cimino et al. | 435/6 |

FOREIGN PATENT DOCUMENTS 0320308 6/1989 European Pat. Off. .

OTHER PUBLICATIONS

National Institutes of Health, "Recombinant DNA Research Guidelines," Fed. Reg. 41:27902 (1976).
National Institutes of Health, "Guidelines for Research Involving Recombinant DNA Molecules," Fed. Reg. 43:60108 (1978).
E. Fisher and D. R. Lincoln, "Assessing Physical Containment in Recombinant DNA Facilities," Recomb. DNA Tech. Bull. 7:1 (1984).
R. W. Old and S. B. Primrose, *Principles of Gene Manipulation*, pp. 167–168 (Univ. of Cal. Press, 2d Ed., 1981).
N. L. Letvin, "Risks of Handling HIV," Nature 349:573 (1991).
T. Maniatis et al., *Molecular Cloning*, pp. 23–24 (Cold Spring Harbor Laboratory, 1982).
P. M. Lizardi et al., "Exponential Amplification of Recombinant RNA Hybridization Probes," Bio/Technol. 6:1197 (1988).
D. L. Kacian et al., "A Replicating RNA Molecule Suitable for a Detailed Analysis of Extracellular Evolution and Replication," Proc. Natl. Acad. Sci. USA 69:3038 (1972).
B. C. F. Chu et al., "Synthesis of an Amplified Reporter DNA for Bioassays," Nucleic Acids Res. 14:5591 (1986).
P. Knight, "Amplifying Probe Assays with Q–beta Replicase," Biotechnol. 7:609 (1989).

(List continued on next page.)

Primary Examiner—W. Gary Jones
Assistant Examiner—Ardin H. Marschel
Attorney, Agent, or Firm—Medlen & Carroll

[57] ABSTRACT

Methods for sterilization of ligase-based amplification products, including products of the Ligation Amplification Reaction (LAR), involving treatment of nucleic acid after amplification to render such nucleic acid incapable of serving as a template for further amplification. Both random and site-specific addition of sterilizing compounds, and more specifically, photoactivation compounds, render amplification product subsequently unamplifiable. Self-sterilizing primers are also employed allowing for a homogenous detection of ligase-based amplification product.

16 Claims, 7 Drawing Sheets

OTHER PUBLICATIONS

D. Y. Wu and R. B. Wallace, "The Ligation Amplification Reaction (LAR)—Amplification of Specific DNA Sequences Using Sequential Rounds of Template–Dependent Ligation," Genomics 4:560 (1989).

U. Landegren et al., "A Ligase–Mediated Gene Detection Technique," Science 241:1077 (1988).

F. Barany, "Genetic Desease Detection and DNA Amplification Using Cloned Thermostable Ligase," Proc. Natl. Acad. Sci USA 88:189 (1991).

S. Kwok and R. Higuchi, "Avoiding False Positives with PCR/" Nature 339:286 (1989).

H. A. Erlich (ed.), *PCR Technology* (Stockton Press, 1989).

K. B. Mullis et al., "Specific Enzymatic Amplification of DNA in vitro: The Polymerase Chain Reaction," Cold Spring Harbor Symposia, LI:263 (1986).

Furrer et al., "Improving PCR Efficiency," Nature 346:324 (1990).

Sarkar et al., "Shedding Light on PCR Contamination," Nature 343:27 (1990).

Cimino et al., "More False–Positive Problems," Nature 345:773 (1990).

C.-Y. Ou, "Use of UV Irradiation to Reduce False Positivity in Polymerase Chain Reaction," BioTechniques 10:442 (1991).

Sarkar et al., "More Light on PCR Contamination," Nature 347:340 (1990).

M. Chamberlin et al., "New RNA Polymerase From *Escherichia coli* Infected with Bacteriophage T7," Nature 228:227 (1970).

S. T. Isaacs et al., "Synthesis and Characterization of New Psoralen Derivatives with Photoreactivity with DNA and RNA," Biochem. 16:1058 (1977).

S. T. Isaacs et al., "A Photochemical Characterization of Reactions of Psoralen Derivatives with DNA," Trends in Photobiology, pp. 279–294 (Plenum Press, 1982).

J. Tessman et al., "Photochemistry of the Furan–Side 8–Methoxypsoralen–Thymidine Monoadduct Inside the DNA Helix. Conversion to Diadduct and to Pyrone–Side Monoadduct," Biochem. 24:1669 (1985).

Webb et al., "Hybridization Triggered Cross–Linking of Deoxyoligonucleotides," Nucleic Acids Res. 14:7661 (1986).

Heikkila et al., "The 9–Fluorenylmethoxycarbonyl (Fmoc) Group for the Protection of Amino Functions of Cytidine, Adenosine, Guanosine and Their 2'–Deoxysugar Derivatives," Acta Chem. Scand. B37:263 (1983).

Beaucage et al., "Deoxynucleoside Phosphoramidites—A New Class of Key Intermediates for Deoxypolynucleotide Synthesis," Tetrahedron Letters 22:1859 (1981).

Gamper et al., "Efficient Formation of a Crosslinkable HMT Monoadduct at the Kpn I Recognition Site," Photochem. Photobiol. 40:29 (1984).

G. Cimino et al., "Wavelength Dependence for the Photoreversal of a Psoralen–DNA Cross Link," Biochem. 25:3013 (1986).

C.-Y. Ou et al., "DNA Amplification for Direct Detection of HIV–1 in DNA of Peripheral Blood Mononuclear Cells," Science 239:295 (1988).

D. A. Erie et al., "Melting Behavior of a Covalently Closed, Single–Stranded Circular DNA," Biochem. 28:268 (1989).

M. C. Longo et al., "Use of Uracil DNA Glycosylase to Control Carryover Contamination in Polymerase Chain Reactions," Gene 93:125 (1990).

The Cetus GeneAmp® PCR Carry–over Prevention Kit Product Insert (1990).

D. Y. Kwoh and T. J. Kwoh, "Target Amplification Systems in Nucleic Acid–Based Diagnostic Approaches," ABL, p. 14 (1990).

"Polymerase Chain Reaction Project Exploring Potential Clinical Applications," p. 1–4, AIDS Research Exchange, U.S. Dept. Health Human Services, Jul./Aug. 1989.

Y. Jinno et al., "Use of Psoralen as Extinguisher of Contaminated DNA in PCR," Nucleic Acids Res. 18:6739 (1990).

R. G. Higuchi and H. Ochman, "Production of Single–Stranded DNA Templates by Exonuclease Digestion Following the Polymerase Chain Reaction," Nucleic Acids Res. 17:5865 (1989).

H. A. Erlich et al., "Recent Advances in the Polymerase Chain Reaction," Science 252:1643 (1991).

J. Fenton–Williams, "Optimization Strategies for the Polymerase Chain Reaction," BioTechniques 7:762 (1989).

P. A. Kichin et al., "Advoidance of False Positives," Nature 344:201 (1990).

R. A. Gibbs and J. S. Chamberlain, "The Polymerase Chain Reaction: A Meeting Report," Genes & Development 3:1095 (1989).

K. B. Mullis, "Applications of the Polymerase Chain Reaction," American Association for Clinical Chemistry, Oct. 26–28, 1988.

B. Furrer et al., "Detection and Identification of *E. coli* Producing Heat–Labile Enterotoxin Type I by Enzymatic Amplification of Specific DNA Fragment," Letters Appl. Microbiol. 10:31 (1991).

S. G. Rogers and B. Weiss, "Exonuclease III of *Escherichia coli* K–12, an AP Endonuclease," Meth. Enzymol. 65:201 (1980).

L.-H. Guo and R. Wu, "New Rapid Methods for DNA Sequencing Based on Exonuclease III Digestion Followed by Base Pair Synthesis," Nucleic Acids Res. 10:2065 (1982).

L.-H. Guo and R. Wu, "Exonuclease III: Use for DNA Sequence Analysis and in Specific Deletions and Nucleotides," Methods in Enzymol. 100:60 (1983).

G. D. Cimino et al., "Psoralens as Photoactive Probes of Nucleic Acid Structure and Function: Organic Chemistry, Photochemistry, and Biochemistry," Ann. Rev. Biochem. 54:1151 (1985).

B. M. Scher et al., "A Possible Effect on the Fate of DNA Ligase Activity Extracted From Differentiating Mouse Erythroleukemia Cells," Cancer Res. 48:6278 (1988).

Y. S. Zhu et al., "The Use of Exonuclease III for Polymerase Chain Reaction Sterilization," Nucleic Acids Res. 19:2511 (1991).

Epicentre Technologies, "Ampligase™ Thermostable DNA Ligase Kit," in 1993 Epicentre Technologies Catalogue, p. 20.

Epicentre Technologies, "GELase™ Enzyme Preparation," in 1993 Epicentre Technologies Catalogue, p. 8.

*Molecular Cloning, A Laboratory Manual,* Maniatis et al. (publ. by Cold Spring Harbor Labs, Cold Spring Harbor, NY, 1982) pp. 387–389.

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

ATAATCCACC TATCCCAGTA GGAGAAAT 28

( 2 ) INFORMATION FOR SEQ ID NO:2:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

ATTTCTCCTA CTGGGATAGG TGGATTATGG GTACCCAAAA AAAAGGGTAC CC 52

( 2 ) INFORMATION FOR SEQ ID NO:3:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GCATTCTGGA CATAAGACAA GGACCAAAGG GTACCCAAAA AAAAGGGTAC CC 52

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

TTTGGTCCTT GTCTTATGTC CAGAATGC 28

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CATTCTTACT ATTTTATTTA ATCCC 25

( 2 ) INFORMATION FOR SEQ ID NO:6:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

ATTTAATCCC 10

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

ATCCTGGGAT TAAAT 15

( 2 ) INFORMATION FOR SEQ ID NO:8:

5,532,146

( i ) SEQUENCE CHARACTERISTICS:
    ( A ) LENGTH: 56 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:8:

```
AAAATAGTAA GAATGTATAG CCCTACCAGC ATTCTGGACA TAAGACAAGG ACCAAA         56
```

( 2 ) INFORMATION FOR SEQ ID NO:9:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
ATCCTGGGAT TAAATAAAAT AGTAAGAATG TATAGCCCTA CCAGCATTCT GGACATAAGA    60
CAAGGACCAA A                                                        71
```

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..19
        ( D ) OTHER INFORMATION: /note="N represents bases in the
            LAR primer seq. (the exact #of bases in the seq.
            is not meant to be indicated)."

( x i ) SEQUENCE DESCRIPTION: SEQ ID NO:10:

```
NNNNNNNNN NNNNNNNNNT ATATT                                          25
```

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 7..23
        ( D ) OTHER INFORMATION: /note="N represents bases in the
            LAR primer seq. (the exact #of bases in the seq.
            is not meant to be indicated)."

( x i ) SEQUENCE DESCRIPTION: SEQ ID NO:11:

```
AATATANNNN NNNNNNNNN NNN                                            23
```

( 2 ) INFORMATION FOR SEQ ID NO:12:

( i ) SEQUENCE CHARACTERISTICS:
        ( A ) LENGTH: 115 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:12:

ATAATCCACC TATCCCAGTA GGAGAAATTT ATAAAGATG GATAATCCTG GGATTAAATA    60

AAATAGTAAG AATGTATAGC CCTACCAGCA TTCTGGACAT AAGACAAGGA CCAAA    115

( 2 ) INFORMATION FOR SEQ ID NO:13:

( i ) SEQUENCE CHARACTERISTICS:
        ( A ) LENGTH: 115 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

TTTGGTCCTT GTCTTATGTC CAGAATGCTG GTAGGGCTAT ACATTCTTAC TATTTATTT    60

AATCCCAGGA TTATCCATCT TTTATAAATT TCTCCTACTG GGATAGGTGG ATTAT    115

( 2 ) INFORMATION FOR SEQ ID NO:14:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

TAGTAAGAAT GT    12

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

AAATAGTAAG AATGT    15

( 2 ) INFORMATION FOR SEQ ID NO:16:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

ACATTCTTAC GATTT    15

METHOD FOR RENDERING LIGASE-BASED AMPLIFICATION PRODUCTS UNAMPLIFIABLE

This is a Continuation of application Ser. No. 07/729,972, filed on Jul. 15, 1991, now abandoned, which is a Continuation-In-Part application of application Ser. No. 07/428,494, filed on Oct. 26, 1989, now U.S. Pat. No. 5,221,608.

FIELD OF THE INVENTION

The invention relates to methods for sterilization of ligase-based amplification products, including products of the Ligation Amplification Reaction (LAR). In particular, the invention involves treatment of nucleic acid after amplification to render such nucleic acid incapable of serving as a template for further amplification.

BACKGROUND OF THE INVENTION

Nucleic acid technology has made possible the manipulation, amplification, selection and characterization of a potentially very large number of eukaryotic, prokaryotic and viral genes. Most importantly, application of nucleic acid techniques allows for the isolation of any nucleic acid sequence within a complex genome, the modification of the sequence, and the introduction of the sequence into diverse species.

With the prospect of advertently or inadvertently releasing nucleic acid sequences into nature that are either a) modified but present in their normal host species, or b) normal but present in a foreign host species, there is some concern that nucleic acid techniques pose a risk to human health. Regulatory approaches to this risk have focused on physical or biological containment of organisms that contain foreign or modified nucleic acid sequences. National Institutes of Health, Federal Register 41:27902 (1976). National Institutes of Health, Federal Register 43:60108 (1978). Such approaches are bolstered by studies that assess the impact of different laboratory protocols and various types of human error and equipment failures on the incidence and extent of uncontained organisms. E. Fisher and D. R. Lincoln, Recomb. DNA Tech. Bull. 7:1 (1984).

With this effort directed at nucleic acids in organisms, little attention has been paid to the problem of naked nucleic acid, i.e., nucleic acid that is free from a host organism. Depending on the particular circumstances, naked nucleic acid can be an infectious or transforming agent. R. W. Old and S. B. Primrose, Principles of Gene Manipulation, pp. 167–168 (Univ. of Cal. Press, 2d Edition 1981). N. L. Letvin, Nature 349:573 (1991). Furthermore, naked nucleic acid can interfere with other laboratory reactions because of carryover.

Carryover

Carryover is broadly defined here as nucleic acid that is accidentally introduced into a reaction mixture. Of course, the types of accidental introductions are numerous. Nucleic acids can be introduced during a spill or because of poor laboratory technique (e.g., using the same reaction vessel or the same pipette twice). Of more concern, however, is the introduction of nucleic acids that occurs even during normal laboratory procedures, including inadvertent transfer from contaminated gloves. As with modified organisms, one of the most troubling source of this type of accident is aerosolization.

Aerosols are suspensions of fine liquid or solid particles, as in a mist. Aerosols can occur by disturbing a solution (e.g., aerosols are created during a spill), but they can also occur simply by disturbing the small amount of material on a container surface (e.g., the residue on the inner surface of a cap of a plastic tube is frequently aerosolized at the moment the tube is opened). Because of the latter, any container having highly concentrated amounts of nucleic acid is a potential source of nucleic acid carryover.

It should be pointed out that the question of whether there is carryover is only significant to the extent that such carryover interferes with a subsequent reaction. In general, any laboratory reaction that is directed at detecting and/or amplifying a nucleic acid sequence of interest among vastly larger amounts of nucleic acid is susceptible to interference by carryover.

Amplification Techniques

The circumstances in the modern laboratory where both a) containers having highly concentrated amounts of nucleic acid are present, and b) reactions directed at amplifying nucleic acid sequences are performed, are relatively common. The screening of genomic DNA for single copy genes is perhaps the best example of procedure involving both concentrated nucleic acid and amplification. There are a number of alternative methods for nucleic acid amplification, including 1) the replication of recombinant phage through lytic growth, 2) amplification of recombinant RNA hybridization probes, 3) the Ligation Amplification Reaction, and 4) the Polymerase Chain Reaction.

1. Recombinant Vectors. Most cloning vectors are DNA viruses or bacterial plasmids with genomic sizes from 2 to approximately 50 kilobases (kb). The amplification of genomic DNA into a viral or plasmid library usually involves i) the isolation and preparation of viral or plasmid DNA, ii) the ligation of digested genomic DNA into the vector DNA, iii) the packaging of the viral DNA, iv) the infection of a permissive host (alternatively, the transformation of the host), and v) the amplification of the genomic DNA through propagation of virus or plasmid. At this point, the recombinant viruses or plasmids carrying the target sequence may be identified. T. Maniatis et al., Molecular Cloning, pp. 23–24 (Cold Spring Harbor Laboratory 1982). Identification of the recombinant viruses or plasmids carrying the target sequence is often carried out by nucleic acid hybridization using plasmid-derived probes.

Bacterial viruses (bacteriophage) can infect a host bacterium, replicate, mature, and cause lysis of the bacterial cell. Bacteriophage DNA can, in this manner, be replicated many fold, creating a large quantity of nucleic acid.

Plasmids are extrachromosomal elements found naturally in a variety of bacteria. Like bacteriophages, they are double-stranded and can incorporate foreign DNA for replication in bacteria. In this manner, large amounts of probes can be made.

The use of plasmid-derived probes for the screening of phage libraries in hybridization reactions avoids the problem of hybridization of vector DNA (e.g., phage-phage, plasmid-plasmid). In the construction of a viral library, it is, therefore, essential that no plasmid DNA be introduced into the phage-genomic DNA mixture. If, for example, 10 picograms of clonable plasmid DNA were introduced into a viral-genomic mixture containing 1 microgram of genomic DNA (0.001% carryover by weight), every 11 clones assessed to contain the target sequence would, on average, represent 10 false positives (i.e., plasmid-plasmid hybridization) and only 1 true positive (probe-target hybridization), assuming a frequency of 1 target insert in $1 \times 10^6$ inserts.

2. Recombinant RNA Probes. P. M. Lizardi et al., Biotechnology 6:1197 (1988), describe recombinant-RNA molecules that function both as hybridization probes and as templates for exponential amplification by QB replicase. Each recombinant consists of a specific sequence (i.e., an "internal probe") within the sequence of MDV-1 RNA. MDV-1 RNA is a natural template for the replicase. D. L. Kacian et al., Proc. Nat. Acad. Sci USA 69:3038 (1972). The recombinant can hybridize to target sequence that is complementary to the internal probe and that is present in a mixture of nucleic acid. Various isolation techniques (e.g., washing) can then be employed to separate the hybridized recombinant/target complex from a) unbound recombinant and b) nucleic acids that are non-complementary to the internal probe. B. C. F. Chu et al., Nucleic Acids Res. 14:5591 (1986). See also Biotechnology 7:609 (1989). Following isolation of the complex, QB replicase is added. In thirty minutes a one-billion fold amplification of the recombinant (i.e., "recombinant RNA probe amplification") occurs, indicating that specific hybridization has taken place with a target sequence.

While a promising technique, recombinant RNA probe amplification works so well that carryover is of particular concern. As little as one molecule of template RNA can, in principle, initiate replication. Thus, the introduction of a single molecule of the amplified recombinant RNA probe into a new reaction vessel can cause RNA to be synthesized in an amount that is so large it can, itself, be a source of further carryover.

3. Ligation Amplification Reaction (LAR). D. Y. Wu and R. B. Wallace, Genomics 4:560 (1989) describe exponential amplification of nucleic acid by sequential rounds of template-dependent ligation. Two sets of oligonucleotides (for a total of four oligonucleotides) are utilized; each set is complementary to one of the strands of target. The primers are added to template. Following heating to create single-stranded template, the mixture is cooled to allow the primers to hybridize to target sequences. The amplification reaction is initiated by the addition of ligase to the reaction mixture and then terminated by raising the temperature (eg. 100° C.) which again creates single-stranded template. The reaction is again cooled to begin the next round. In each round or cycle, the adjacent oligonucleotides are ligated. The ligase joins the oligonucleotides by the formation of a phosphodiester bond, provided they are correctly base-paired with the target strand at the point of ligation. See U. Landegren et al. Science 241:1077 (1988). The products of the ligation reaction serve as templates for subsequent ligation reactions.

F. Barany, Proc. Nat. Acad. Sci. 88:189 (1991) describes a thermally stable ligase for LAR. This allows for cycling without the need to add additional enzyme for each round of ligation. This also allows for the use of temperatures near the oligonucleotide $T_m$, enhancing the specificity of the reaction. For example, the mixture of template and primers can be heated in the presence of ligase for one minute at 94° C. and then cooled to 65° C. for four minutes, to allow for hybridization and ligation. This cycle can be repeated many times to allow for denaturation, hybridization and ligation.

Thermostable ligase is now available commercially (Epicentre Technologies, Madison, Wis.). With these improvements, LAR will likely become a more widely used amplification reaction.

As with the other amplification reactions discussed herein, LAR will also have the problem of carryover. Since the ligation products serve as template for further ligation, false signals can be expected when the ligation product from a previous reaction gets into the reaction mixture for a subsequent LAR.

4. Polymerase Chain Reaction. K. B. Mullis et al., U.S. Pat. Nos. 4,683,195 and 4,683,202, describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers are then permitted to annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle;" there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to by the inventors as the "Polymerase Chain Reaction" (hereinafter PCR). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labelled probe; incorporation of biotinylated primers followed by avidin-enzyme conjugate detection; incorporation of $^{32}P$ labelled deoxynucleotide triphosphates, e.g., dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

The PCR amplification process is known to reach a plateau concentration of specific target sequences of approximately $10^{-8}M$. A typical reaction volume is 100 µl, which corresponds to a yield of $6 \times 10^{11}$ double stranded product molecules. At this concentration, as little as one femtoliter ($10^{-9}$ microliter) of the amplified PCR reaction mixture contains enough product molecules to generate a detectable signal in a subsequent 30 cycle PCR amplification. If product molecules from a previous PCR are carried over into a new PCR amplification, it can result in a false positive signal during the detection step for the new PCR reaction.

Handling of the reaction mixture after PCR amplification can result in carryover such that subsequent PCR amplifications contain sufficient previous product molecules to result in a false positive signal. S. Kwok and R. Higuchi, Nature 339, 286 (1989). PCR Technology, H. A. Erlich (ed.)

(Stockton Press 1989). This can occur either through aerosols or through direct introduction, as described above for other types of carryover.

Control of Carryover

Various approaches to controlling carryover have been reported in the literature. Literature references below are made without any intention to admit that they constitute prior art relative to the claimed invention. All rights to claim that the subject invention was invented prior to references referred to herein is expressly reserved.

At present, there are three approaches for the control of carryover. These can be broadly defined as: 1) containment, 2) elimination, and/or 3) prevention. With the containment approach, amplification is performed in a closed system. Usually, this means a designated part of the laboratory that is closed off from all other space. Of course, the designated area must be appropriately configured for the particular amplification assay. In the case of replication of recombinant phage through lytic growth, the area must allow for the amplification of the genomic DNA through propagation of virus or plasmid. The area must also provide all the requisite equipment and reagents for amplification and subsequent detection of the amplified segment of the target sequence.

The problem with containment is that it is very inconvenient. In order for the containment area to be configured to provide conditions appropriate for all the steps of amplification, the laboratory must commit a separate set of equipment. This duplicate set of equipment, furthermore, is also subject to carryover. Over time it can be rendered unusable.

The elimination approach is used when carryover has already occurred. New stocks of enzymes, buffers, and other reagents are prepared along with a complete and thorough cleaning of the laboratory area where amplification is performed. All surfaces are scrubbed and all disposable supplies replaced. Suspect laboratory equipment is either discarded or removed from the area.

The elimination approach is also unsatisfactory. First, it does not entirely render the area free of carryover. Indeed, the cleaning process can, itself, generate aerosols. Second, the level of thoroughness needed in the cleaning requires too much time. Finally, it is not practical to constantly be discarding or removing laboratory equipment.

One preventative approach to dealing with plasmid carryover in phage libraries is the purification of the probe. Purifying the probe so that it is essentially free of plasmid DNA can reduce the incidence of plasmid-plasmid hybridization.

There are a number of problems with this approach. First, while reducing the incidence of plasmid-plasmid hybridization, this method leaves the carryover in the library. Second, purification is never 100%; the method can only reduce, not eliminate, the problem. This carryover is an inherent problem with all cloning vectors including not only bacterial viruses and plasmids, but also animal and plant viruses and plasmids as well as the more recent technologies such as yeast chromosomal vectors.

There is at present one preventative approach to dealing with recombinant-RNA probe carryover. This involves base treatment to destroy RNA carryover. This approach will not harm DNA target. However, it is obviously inadequate as a treatment for RNA target.

One prevention method for PCR carryover that has been considered up to now involves the use of nested primers. While originally applied to PCR to improve specificity, the nested primer technique can also be applied to PCR as a means of reducing the problem of carryover. Nested primers are primers that anneal to the target sequence in an area that is inside the annealing boundaries of the two primers used to start PCR. K. B. Mullis et al., Cold Spring Harbor Symposia, Vol. LI, pp. 263–273 (1986). When applied to the carryover problem, nested primers are used that have non-overlapping sequences with the starting primers. Because the nested primers anneal to the target inside the annealing boundaries of the starting primers, the predominant PCR-amplified product of the starting primers is necessarily a longer sequence than that defined by the annealing boundaries of the nested primers. The PCR amplified product of the nested primers is an amplified segment of the target sequence that cannot, therefore, anneal with the starting primers. If this PCR-amplified product of the nested primers is the nucleic acid carried over into a subsequent PCR amplification, the use of the starting primers will not amplify this carryover.

There are at least two problems with the nested primer solution to carryover in PCR reactions. First, the carryover is neither removed, nor inactivated (inactivation is defined as rendering nucleic acid unamplifiable in PCR). Second, the amplified product of the nested primers will be amplified if the same nested primers are used in a subsequent PCR.

Of course, another solution to carryover in subsequent PCR amplifications is to use different primers altogether. This is not, however, a practical solution. First, making new primers for every new PCR amplification would be extremely time consuming and costly. Second, PCR amplification with each primer pair must be individually optimized. Third, for a target sequence of a given length, there is a limit to the number of non-overlapping primers that can be constructed.

Others have proposed pre-amplification sterilization techniques in which background nucleic acid is rendered unamplifiable prior to addition of the template. For example Furrer et al. in Nature Vol. 346, p. 324 (1990) refers to a sterilization approach employing DNaseI or restriction enzymes to digest background nucleic acid prior to adding template and Taq DNA polymerase. A principal problem with this approach is that it requires opening the reaction container after sterilization in order to add the template. Thus, an additional opportunity for carryover is created after sterilization and prior to amplification. Given the extreme sensitivity of PCR, the consequences of this flaw could be drastic.

Another pre-amplification sterilization approach has been proposed which utilizes ultraviolet irradiation prior to amplification. Sarkar et al., Nature, Vol. 343, p.27 (Jan. 4, 1990). There are several problems with this approach. Cimino et al., Nature, Vol. 345, pp. 773, 774, (Jun. 28, 1990). First, target DNA and Taq polymerase must be introduced after irradiation, which will produce the same level of sporadic false-positive PCR signals even though all the contaminating carryover molecules in the other PCR reagent are sterilized. Second, Sarkar et al.'s conclusion that the oligonucleotide primers for the PCR retain their full functional integrity after irradiation is not warranted. C. -Y. Ou, BioTechniques 10:442 (1991). Primer damage which leads to a compromise in signal sensitivity can be evaluated only when the PCR amplification is limited so that the concentration of product is maintained well below PCR plateau concentrations. Finally, Sarkar et al.'s approach does not address the critical nature of the size and sequence specificity of the PCR product being inactivated. Some of the limitations of this approach were subsequently acknowledged by Sarkar et al. Nature, 347:340, 351 (1990)

SUMMARY OF THE INVENTION

The problems discussed above, including but not limited to the need to control carryover in LAR, are solved by the methods of the present invention. The present invention provides a method for sterilizing ligase-based amplification product, comprising the sequential steps of a) providing, in any order, i) one or more sterilizing compounds, ii) one or more primers, iii) sample template, iv) amplification reagents, v) at least one enzyme having ligase activity, and vi) means for containing a reaction; b) adding to said reaction containing means, in any order, said one or more sterilizing compounds, said sample template, said one or more primers and said amplification reagents, to make a reaction mixture; c) adding said enzyme having ligase activity to said reaction mixture to create ligase-based amplification product; and d) treating said mixture such that said sterilizing compound renders said ligase-based amplification product subsequently unamplifiable.

In one embodiment the method further comprises, immediately after said adding of said enzyme having ligase activity, the step of closing said reaction containing means. It is preferred that the reaction containing vessel is maintained in a closed condition until the completion of step d) above.

In another embodiment, the method further comprises, after step d), the step of detecting said unamplifiable, ligase-based amplification products.

In a preferred embodiment, the method employs primers containing synthetically introduced A:T tails. It is contemplated that such regions increase the efficiency of sterilization by i) lengthening the primers (and, therefore, lengthening the product of amplification), and ii) by providing preferred binding sites for certain sterilizing compounds.

The present invention contemplates performing the method wherein said sterilizing compound is an activation compound. More specifically, it is contemplated that the activation compound is a photoactivation compound. The preferred photoreactive compound is a psoralen, such as 4'-aminomethyl- 4,5', 8-trimethylpsoralen (AMT) or 4'-hydroxymethyl- 4,5', 8-trimethylpsoralen (HMT)

The present invention also contemplates sterilization utilizing site-specifically added sterilizing compounds. In one embodiment, the present invention contemplates a method for sterilizing ligase-based amplification product, comprising the sequential steps of a) providing, in any order, i) one or more primers containing synthetically introduced crosslinking compounds, ii) sample template, iii) amplification reagents, iv) at least one enzyme having ligase activity, and v) means for containing a reaction; b) adding to said reaction containing means, in any order, said one or more primers, said sample template, and said amplification reagents, to make a reaction mixture; c) adding said enzyme having ligase activity to said reaction mixture to create ligase-based amplification product; and d) treating said mixture such that said crosslinking compounds on said one or more primers renders said ligase-based amplification product subsequently unamplifiable.

The present invention also contemplates a method for sterilizing ligase-based amplification product without sterilizing compounds. In this method, sterilization comprises the sequential steps of a) providing, in any order, i) one or more self-sterilizing primers, comprising a self-hybridizing region having a $T_m$ ii) sample template, iii) amplification reagents, iv) at least one enzyme having ligase activity, and v) means for containing a reaction; b) adding to said reaction containing means, in any order, said one or more self-sterilizing primers, said sample template, said amplification reagents, to make a reaction mixture; c) adding said enzyme having ligase activity to said reaction mixture, at a temperature above said $T_m$ of said self-hybridizing region of said self-sterilizing primer, to create ligase-based amplification product; and d) cooling said reaction mixture to a temperature at or below said $T_m$ of said self-hybridizing region of said self-sterilizing primer, so that said ligase-based amplification product is rendered subsequently unamplifiable.

In one embodiment of this method, it is desired, immediately after said adding of said enzyme having ligase activity, that the reaction containing means is closed and that the reaction containing vessel is maintained in a closed condition until the completion of step d).

The present invention also contemplates a homogenous detection scheme in conjunction with the use of self-sterilizing primers. This schmeme comprises, after step d), the detecting of said unamplifiable, ligase-based amplification products, comprising the sequential steps of i) enzymatically digesting all nucleic acid in said reaction mixture except said unamplifiable, ligase-based amplification products, and ii) adding a reporter molecule to said reaction mixture.

In one embodiment said enzymatic digestion is performed using Exonuclease III and said reporter molecule comprises a fluorescent intercalator, such as ethidium bromide.

BRIEF DESCRIPTION OF THE FIGURES

FIG. 6 shows the sequences (SEQ ID NOS: 4–9) used for site-specific addition.

DEFINITIONS

Figure 1:
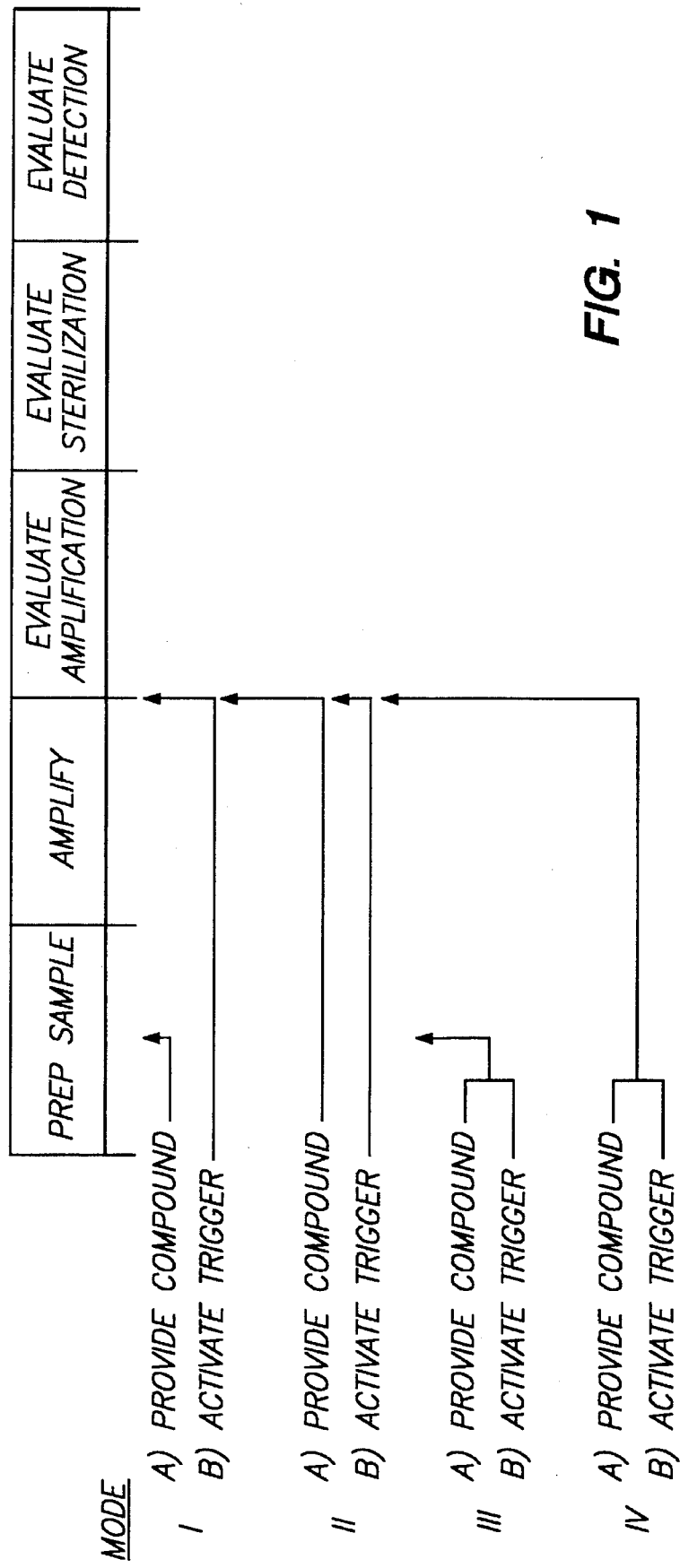
FIG. 1 schematically outlines the methods by which activation compounds can be screened for use as sterilizing compounds.

The following definitions are intended for use in interpreting the claims and the specification. The definitions are intended to supersede any differing or contrary definitions which may be commonly used in the art. The definitions are not intended to operate as admissions of what is or is not prior art.

A. Reactants

"Template" is defined as the nucleic acid sequence from which a complementary nucleic acid or protein molecule is enzymatically synthesized. In the case of replication, nucleic acid polymerases replicate a nucleic acid molecule ("template") to yield a complementary ("daughter") nucleic acid molecule. For example, DNA polymerase I, isolated from *E. coli*, catalyzes the addition of deoxyribonucleoside triphosphates to the 3' end of a short segment of DNA ("primer") hybridized to a template strand to yield a daughter of the template, starting from a mixture of precursor nucleotides (dATP, dGTP, dCTP, and dTTP). This 5' to 3' template-dependent enzymatic synthesis is also called "primer extension." The reaction will not take place in the absence of template. The reaction can be measured if one or more of the precursor nucleotides are labelled (usually they are radiolabelled with $^{32}$P). "Template" may refer to nucleic acid containing one or more segments of one or more targets (defined below), or nucleic acid containing no target. "Template" may also be nucleic acid containing one or more replicatable probes, or nucleic acid containing no replicatable probes.

"Template" encompasses both the situation where the nucleic acid contains one or more segments of one or more target sequences, and the situation where the nucleic acid contains no target sequence (and, therefore, no segments of target sequences). Where template containing target sequences is used for amplification and amplification is carried out, there is "amplification product."

"Target" is a nucleic acid sequence, usually comprising a portion of a larger nucleic acid molecule, which an investigator seeks to sort out from other nucleic acid. Amplification techniques have been designed primarily for this sorting out. A particular set of primers in an amplification reagent (defined below) is target-specific. Target may be found in a nucleic acid sample for which the objective is to use an amplification technique, such as LAR for example, to "find" and "copy" the target.

"Amplification" is a special case of replication involving template specificity. (As noted above, replication is one type of "template-dependent enzymatic synthesis"). Amplification is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity.

The present invention provides "sterilizing compounds" and methods for using "sterilizing compounds." "Sterilizing compounds" are defined such that, when used to treat nucleic acid according to the sterilization method of the present invention, the nucleic acid is rendered substantially unamplifiable, i.e., substantially sterilized. The preferred sterilizing compounds of the present invention are activation compounds.

Template specificity is achieved in most amplification techniques by the choice of enzyme. Amplification enzymes are enzymes that, under the conditions they are used, will process only specific sequences of nucleic acid in a heterogenous mixture of nucleic acid. For example, in the case of Qβ replicase, MDV-1 RNA is the specific template for the replicase. D. L. Kacian et al., Proc. Nat. Acad. Sci USA 69:3038 (1972). Other nucleic acid will not be replicated by this amplification enzyme. Similarly, in the case of T7 RNA polymerase, this amplification enzyme has a stringent specificity for its own promoters. M. Chamberlin et al., Nature 228:227 (1970). In the case of T4 DNA ligase, the enzyme will not ligate the two oligonucleotides where there is a mismatch between the oligonucleotide substrate and the template at the ligation junction. D. Y. Wu and R. B. Wallace, Genomics 4:560 (1989). Finally, Taq polymerase, by virtue of its ability to function at high temperature, is found to display high specificity for the sequences bounded and thus defined by the primers; the high temperature results in thermodynamic conditions that favor primer hybridization with the target sequences and not hybridization with non-target sequences. PCR Technology, H. A. Erlich (ed.) (Stockton Press 1989).

"Amplification reagents" are defined as those reagents (buffers, salts, etc.) needed for amplification. These reagents are exclusive of nucleic acid (primers, template etc.) and the amplification enzyme.

B. Template Sources

"Sample" is defined as a representative part of a larger whole or group that is provided for determining the presence of target. It may be biological (e.g., blood, urine, hair, etc.), experimental (e.g., reaction products, chemical synthesis products, purified extracts, etc.), or industrial (e.g., waste, solvents, processed food, etc.). The nucleic acid may be RNA or DNA.

A sample may or may not contain nucleic acid. It may or may not contain "sample template" and/or "background template".

"Sample template" is defined as the nucleic acid originating from the sample which is to be analyzed for the presence of target. Sample template may originate from the sample in the manner that nucleic acid from a blood sample originates from the cells of the blood. On the other hand, it may originate from the sample because the sample is infected (e.g., viral nucleic acid in a blood sample).

"Background template" is defined as nucleic acid, other than sample template, found in the sample. Background template is inadvertent. For example, it may include carryover from previous amplification reactions. On the other hand, it may include nucleic acid contaminants sought to be purified away from the sample. "Background signal" refers to an assay signal which is due to the presence of background template or its amplification product.

A "base" refers to a monomeric unit of nucleic acid. Technically, the monomeric units of DNA are called "deoxyribonucleotides" and those of RNA are "ribonucleotides". Each nucleotide is comprised of 1) a nitrogenous heterocyclic base, 2) a pentose, and 3) a molecule of phosphoric acid. Since the nucleotide is distinguished by the type of base, however, a shorthand reference for nucleotide has evolved; the nucleotide is simply referred to as a "base".

C. Sterilization

"Sterilization" is defined as the rendering of nucleic acid incapable of replication, so as to prevent said nucleic acid from being amplified and subsequently detected by a particular assay protocol. While the term "sterilization" has typically been applied only in the context of living organisms, it is here meant to be applied to in vitro amplification protocols of polynucleotides where a template polynucleotide functions in the nature of a germination seed for its further propagation.

Sterilization "sensitivity" is an operationally defined term. It is defined only in the context of a "sterilization method" and the particular detection method that is used to measure templates (or organisms). Sterilization sensitivity is the number of germination seeds (e.g., viable bacterial cells or polynucleotide templates) that result in a measurable signal in some sterilization method and defined detection assay.

A "substantial portion" of nucleic acid is sterilized when, upon amplification, there is no measurable signal as a result of the amplification of the nucleic acid. (Similarly, a "substantial portion" of nucleic acid molecules are hydrolyzed when, upon amplification, there is no measurable signal.)

"Sterilizing reagents" are defined as chemicals which, when used to treat nucleic acid according to a sterilization method, render background nucleic acid substantially unamplifiable, i.e., substantially sterilized.

"Post-amplification sterilization" as described and claimed in U.S. Pat. No. 5,184,020 issued to Hearst et al., on Feb. 2, 1993, U.S. Pat. No. 5,139,940, issued to Isaacs et al., on Aug. 18, 1992, and U.S. Pat. No. 5,221,608, issued to Cimino et al., on Jun. 22, 1993 each of which are hereby incorporated by reference, is defined by the timing of the sterilization event; in post-amplification sterilization the amplification product is sterilized after amplification and prior to a potential carryover event. Conversely, in preamplification sterilization background template, possibly including amplification product from a previous reaction, is rendered unamplifiable before an amplification reaction, but after the potential carryover event.

DESCRIPTION OF THE INVENTION

The description of the invention is divided into I) Sterilization, II) Compound Synthesis, III) Binding Compounds to Nucleic Acid, IV) Crosslinking, and IV) Design and Use of Self-Sterilizing Primers.

I. Sterilization

Something is "sterilized" when it is rendered incapable of replication. While the term "sterilization" has typically been applied only in the context of living organisms, it is here meant to be applied to in vitro amplification protocols of polynucleotides where a template polynucleotide functions in the nature of a germination seed for its further propagation.

A. Sensitivity

Sterilization "sensitivity" is an operationally defined term. It is defined only in the context of a "sterilization method" and the particular detection method that is used to measure templates (or organisms). Sterilization sensitivity is the number of germination seeds (e.g., viable bacterial cells or polynucleotide templates) that result in a measurable signal in some sterilization method and defined detection assay.

To appreciate that a "sterilization method" may or may not achieve "sterilization," it is useful to consider a specific example. A bacterial culture is said to be sterilized if an aliquot of the culture, when transferred to a fresh culture plate and permitted to grow, is undetectable after a certain time period. The time period and the growth conditions (e.g., temperature) define an "amplification factor". This amplification factor along with the limitations of the detection method (e.g., visual inspection of the culture plate for the appearance of a bacterial colony) define the sensitivity of the sterilization method. A minimal number of viable bacteria must be applied to the plate for a signal to be detectable. With the optimum detection method, this minimal number is 1 bacterial cell. With a suboptimal detection method, the minimal number of bacterial cells applied so that a signal is observed may be much greater than 1. The detection method determines a "threshold" below which the "sterilization method" appears to be completely effective (and above which "sterilization" is, in fact, only partially effective). This interplay between the amplification factor of an assay and the threshold that the detection method defines, can be illustrated. Referring now to Table 1, bacterial cells are applied to a plate under two different sets of conditions: in one case, the growth conditions and time are such that an overall amplification of $10^4$ has occurred; in the other case, the growth conditions and time are such that an overall amplification of $10^8$ has occurred. The detection

TABLE 1

| AMPLIFICATION FACTOR | # OF VIABLE BACTERIAL CELLS APPLIED TO A PLATE | | | | |
| --- | --- | --- | --- | --- | --- |
| | 1 | 10 | 100 | 1000 | |
| $10^4$ | $10^4$ | $10^5$ | $10^6$ | $10^7$ | # of Bacterial cells after Amplification |
| | − | − | + | ++ | Detection (+/−) |
| $10^8$ | $10^8$ | $10^9$ | $10^{10}$ | $10^{11}$ | # of Bacterial cells after Amplification |
| | ++ | +++ | +++ | ++++ | Detection (+/−) | method is arbitrarily chosen to be visual inspection. The detectable signal will be proportional to the number of bacterial cells actually present after amplification. For calculation purposes, the detection threshold is taken to be $10^6$ cells; if fewer than $10^6$ cells are present after amplification, no cell colonies are visually detectable and the sterilization method will appear effective. Given the amplification factor of $10^4$ and a detection threshold of $10^6$, the sterilization sensitivity limit would be 100 bacterial cells; if less than 100 viable bacterial cells were present in the original aliquot of the bacterial culture after the sterilization method is performed, the culture would still appear to be sterilized. Alternatively, if the time and growth conditions permitted an amplification of $10^8$, then the sterilization sensitivity limit (assuming the same detection threshhold) would be 1 bacterial cell. Under the latter conditions, the sterilization method must be sufficiently stringent that all bacterial cells are, in fact, incapable of replication for sterilization to appear complete (i.e., the sterilization method would need to cause sterilization, not just substantial sterilization).

B. Carryover

The same considerations of detection threshold and amplification factor are present when determining the sensitivity limit of a sterilization method for nucleic acid. Again, by "sterilization" it is meant that the nucleic acid is rendered incapable of replication, and specifically, unamplifiable.

The post-amplification sterilization method of the present invention renders nucleic acid substantially unamplifiable. In one embodiment, the post-amplification sterilization method renders amplified nucleic acid unamplifiable but detectable. In still another embodiment, the post-amplification sterilization method of the present invention contemplates that the number of carryover molecules of amplifiable nucleic acid that has occurred is small enough that, in a subsequent amplification, any amplified product reflects the presence of true target in the sample. In a preferred embodiment, the post-amplification sterilization method of the present invention renders amplified segments of a target sequence substantially unamplifiable but detectable prior to a carryover event.

Post-amplification sterilization is designed to control carryover. It is desirable to concurrently run reagent controls to assure that carryover is absent in the first place.

C. Selecting Activation Compounds

The present invention provides "sterilizing compounds" and methods for using "sterilizing compounds." "Sterilizing compounds" are defined such that, when used to treat nucleic acid according to the sterilization method of the present invention, the nucleic acid is rendered substantially unamplifiable, i.e., substantially sterilized.

The preferred sterilizing compounds of the present invention are activation compounds. "Activation compounds" defines a family of compounds that undergo chemical change in response to triggering stimuli. Triggering stimuli include, but are not limited to, thermal stimuli, chemical stimuli and electromagnetic stimuli. "Photoreactive, activation compounds" (or simply "photoreactive compounds"), defines a genus of compounds (Table 2)

TABLE 2

Photoreactive Compounds

Actinomycins
Anthracyclinones
Anthramycin
Benzodipyrones
Fluorenes and fluorenones
Furocoumarins
Mitomycin
Monostral Fast Blue
Norphillin A
Organic dyes
Phenanthridines
Phenazathionium salts
Phenazines
Phenothiazines
Phenylazides
Polycyclic hydrocarbons
Quinolines
Thiaxanthenones in the activation compound family that undergo chemical change in response to electromagnetic radiation. FIG. 1 outlines the methods by which activation compounds can be screened for use as sterilizing compounds. Four "Sterilization Modes" are shown along with the temporal points where potential reactants of each Mode are added to the amplification system (the amplification system is contemplated to encompass all amplification methods, e.g., target-amplifying or probe-amplifying).

The Sterilization Modes consist of the following temporal steps:

Mode I: Add activation compound then amplify sample, followed by activation ("triggering") of the activation compound Mode II: Amplify sample then add activation compound, followed by activation ("triggering") of the activation compound Mode III: Add pre-activated ("triggered") activation compound then amplify sample Mode IV: Amplify sample then add pre-activated ("triggered") activation compound In the general case, an activation compound is "triggered" to an active form. This form provides the sterilizing activity to the system. The type of triggering required depends on the properties of the sterilizing compound. For example, thermally reactive compounds are triggered by providing the correct temperature while photoreactive compounds are triggered by providing the appropriate activating wavelengths of electromagnetic radiation. Thoughtful consideration of FIG. 1 allows any activation compound to be analyzed as a potential sterilizing compound and defines its appropriate Mode of application (if any).

A new compound ("X") can be evaluated as a potential sterilizing compound (see Table 3). X is initially evaluated in Step A of Mode I. In Step A, X is added to the sample during the sample preparation step prior to amplification. The amplification process is performed and the yield of the amplified product compared to an identical sample amplified without X. If the amplification yield is similar in both samples, the sterilization activity of X is evaluated in Step B of Mode I. In Step B, the appropriate "trigger" is pulled to activate X after amplification has occurred. For example, if X is a thermal reagent, the appropriate temperature is provided to generate the activated form of the compound (X*=generically activated X). The sterilization effect of X* on the amplified products is then determined by reamplification of the amplified products after treatment. If an acceptable level of sterilization is realized, a separate evaluation is performed to determine the effect of the modification provided by X* on subsequent detection of the modified target molecules. In this manner, both the effectiveness of X as a Mode I sterilization reagent and the compatibility of the modified amplified target with subsequent detection formats is evaluated.

Alternatively, X may inhibit the amplification process in Mode I, Step A. In this event, X cannot be effectively used in Mode I; X is thereafter evaluated as a Mode II sterilization reagent. In Mode II, the temporal order of amplification, compound addition and triggering are changed relative to Mode I. X is added following amplification in Mode II, thereby avoiding the amplification inhibition detected in Mode I. In this fashion, the sterilization effect of X* on the amplified products can be determined independent of the negative effect of X on amplification. Evaluation of the Mode II sterilization activity is done in the same fashion as for Mode I, Step B.

The two additional methods which use X for sterilization are Modes III and IV. In both these Modes, X is triggered to provide X, prior to addition to the sample. X* is then added to the system either before (Mode III) or after (Mode IV) amplification.

In Mode III, X* may be provided then added to the sample prior to amplification. In the case where X is a photoreactive compound, X* is the resultant product of the exposure of photoreactive compound to activating wavelengths of electromagnetic radiation. If amplification is inhibited with this resultant product, it may reasonably be suspected that exposure of X to activating wavelengths of electromagnetic radiation results in photoproduct.

In Mode IV, X* is provided then added to the system following amplification, thereby avoiding any issue of compatablity with the amplification process. X*, whether a thermally activated or photoactivated, when provided and used according to Mode IV, can provide effective sterilization via more than one mechanism. X* may react with amplified target, non-nucleic acid components of the system, or both.

Environmental factors are important considerations—particularly during sample preparation. The preferred compound will not require special handling due to toxicity or sensitivity to the normal laboratory/clinical environment, including the normal incandescent or fluorescent lighting found in such environments. Compounds which are toxic to the user and/or sensitive to room light will require

TABLE 3

EVALUATION OF POTENTIAL STERILIZATION REAGENTS

| Mode/Step | Result* | Interpretation/Next Step |
|---|---|---|
| I/A | + ampl | Compound is compatible with amplication/Evaluate in Mode I, Step B |
| I/A | − ampl | Compound is incompatible |

TABLE 3-continued

EVALUATION OF POTENTIAL STERILIZATION REAGENTS

| Mode/Step | Result* | Interpretation/Next Step |
|---|---|---|
| | | with amplication/Evaluate in Mode II, Steps A and B |
| I/A + B | + ster | Compound is a useful sterilization reagent in Mode I/Evaluate detection |
| I/A + B | − ster | Compound is ineffective as a sterilization reagent in Mode I/Evaluate in Modes II, III and IV |
| II | + ster | Compound is useful for sterilization in Mode II/Evaluate detection |
| II | − ster | Compound is ineffective as a sterilization reagent in Mode II/Evaluate in Modes III and IV |
| III | − ampl | Compound may be useful in Mode IV. |
| III | + ampl | Compound is compatible with amplification but not useful for sterilization by definition. |
| IV | + ster | Compound is a useful sterilization reagent in Mode IV/Evaluate detection |
| IV | − ster | Compound is an ineffective as a sterilization reagent in Mode IV. |

*+/− ampl = amplifiation inhibited/amplifiation not inhibited
+/− ster = sterilization effective/sterilization ineffective a special environment for use. Special environments make the assay inherently more cumbersome and complex and correspondingly more subject to error. The supporting instrumentation for such assays likewise becomes more complicated.

Because it is desired that amplified nucleic acid not be exposed to the environment until they are sterilized, a preferred embodiment of the present invention contemplates the use of photoreactive compounds for sterilization. As noted earlier, "photoreactive compounds" are defined as compounds that undergo chemical change in response to appropriate wavelengths of electromagnetic radiation. Photoreactive compounds possess the advantage of allowing inactivation without opening the reaction vessel (when appropriate reaction vessels are used). Furthermore, because it is desired that the modification of the amplified nucleic acid not interfere with subsequent steps, the present invention contemplates the use of photoreactive compounds that do not interfere with detection.

In the preferred embodiment, the invention contemplates amplifying and sterilizing in a closed system, i.e., the amplified nucleic acid is not exposed to the environment until modified. In one embodiment, the present invention contemplates having the photoreactive compound present in the reaction mixture during amplification. In this manner, the reaction vessel need not be opened to introduce the sterilizing compound.

The use of photoreactive compounds in closed containers requires that sufficient light of appropriate wavelength(s) be passed through the vessel. Thus, a light instrument must be used in conjunction with the present invention to irradiate the sample. A commercially available instrument for this purpose is the HRI-100.

II. Compound Synthesis

The present invention contemplates sterilization using activation compounds, and in particular, photoreactive compounds. "Photoreactive compounds" defines a genus of compounds that undergo chemical change in response to electromagnetic radiation. One species of photoreactive compounds described herein is commonly referred to as furocoumarin. The furocoumarins belong to two main categories: 1) psoralens [7H-furo(3,2-g)-1-benzopyran-7-one, or δ-actone of 6-hydroxy-5-benzofuranacrylic acid], which are linear:

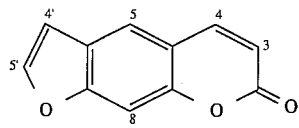

and in which the two oxygen residues appended to the central aromatic moiety have a 1, 3 orientation, and further in which the furan ring moiety is linked to the 6 position of the two ring coumarin system, and 2) the isoporalens [2H-furo(2,3-h)-1-benzopyran-2-one, or δ-lactone of 4-hydroxy-5-benzofuranacrylic acid], which are angular:

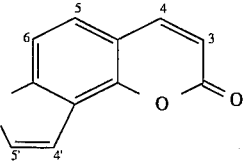

in which the two oxygen residues appended to the central aromatic moiety have a 1, 3 orientation, and further in which the furan ring moiety is linked to the 8 position of the two ring coumarin system. Psoralen derivatives are derived from substitution of the linear furocoumarin at the 3, 4, 5, 8, 4', or 5' positions, while isopsoralen derivatives are derived from substitution of the angular furocoumarin at the 3, 4, 5, 6, 4', or 5 positions.

The synthesis of psoralens is well-described. S. T. Isaacs et al., Biochemistry 16:1058 (1977). S. T. Isaacs et al., Trends in Photobiology (Plenum) pp. 279–294 (1982). J. Tessman et al., Biochem. 24:1669 (1985). Hearst et al., U.S. Pat. Nos. 4,124,589, 4,169,204 and 4,196,281, hereby incorporated by reference, describe synthesis methods for psoralens that are useful in conjunction with the present invention.

III. Binding of Compounds to Nucleic Acid

In one embodiment, the present invention contemplates sterilization of ligase-based amplification by binding activation compounds to amplification product. In such a case, it is contemplated that the amplification product is thereafter unable to serve as target sequences for further amplification.

As noted above, target sequences are regions of nucleic acid having one or more segments of known base sequence. Target sequences are "targets" in the sense that they are sought to be sorted out from other nucleic acid. In the case of LAR, target sequences are sorted out by hybridization with LAR primers. LAR primers are nucleic acids having a base sequence that is partially or completely complementary with all or a portion of a target sequence.

The present invention contemplates that the binding to all these forms of nucleic acid (as well as others) can be non-covalent binding and/or covalent binding. The present invention contemplates specific embodiments of binding including, but not limited to dark binding and photobinding.

A. Dark Binding

One embodiment of the binding of the present invention involves dark binding. "Dark Binding" is defined as binding to nucleic acid that occurs in the absence of photoactivating wavelengths of electromagnetic radiation. Dark binding can be covalent or non-covalent. "Dark Binding Compounds" are defined as compounds that are capable of dark binding. In one embodiment, the dark binding of the present invention involves the steps: a) providing a dark binding compound; and b) mixing the dark binding compound with nucleic acid in the absence of photoactivation wavelengths of light, so that the dark binding compound binds to the nucleic acid. The present invention further contemplates the product of dark binding, i.e., a dark binding compound-:nucleic acid complex.

The present invention also contemplates dark binding of photoproduct. "Photoproduct" is defined as a product of the reaction of a compound and activating wavelengths of electromagnetic radiation that, once formed, is later capable of binding to nucleic acid in the absence of electromagnetic radiation.

In considering photoproduct binding, it should be noted that previous work towards the modification of nucleic acids with furocoumarins has historically proceeded by a method having the temporal steps: 1) providing a specific furocoumarin derivative, 2) providing a particular nucleic acid or nucleic acid sequence, and 3) mixing the furocoumarin with the nucleic acid in the presence of activating wavelengths of electromagnetic radiation. Depending on the details of the particular reaction, including the particular furocoumarin derivative, radiation source irradiation time, buffer, temperature and other factors used for the procedure, a given level of covalent modification, with almost exclusively cyclobutyl type 2+2 photocycloaddition products, resulted.

In one embodiment, the present invention contemplates a radical departure from this historical approach to photobinding. In one embodiment of the method of the present invention, the temporal sequence is the following: 1) providing one or more furocoumarin derivatives, 2) exposing the furocoumarin derivative(s) to activating wavelengths of electromagnetic radiation, 3) providing a particular nucleic acid sample or nucleic acid sequence, and 4) mixing the irradiated furocoumarin derivative(s) with the nucleic acid in the absence of activating wavelengths of electromagnetic radiation. In this embodiment, the furocoumarin derivative is irradiated prior to mixing with nucleic acid. The experimental investigation of this novel temporal sequence has established the existence of furocoumarin photoproduct. Application of the novel temporal sequence has useful applications but was neither predicted nor expected from the chemical or biochemical literature concerning furocoumarins.

"Photoproduct" is best understood by considering the possible reactions of photoreactive compound when exposed to activating wavelengths of electromagnetic radiation. While not limited to any precise mechanism, it is believed that the reaction of photoreactive compound in its ground state ("C") with activating wavelengths of electromagnetic radiation creates a short-lived excited species ("C*"):

C→C*

What happens next is largely a function of what potential reactants are available to the excited species. Since it is short-lived, a reaction of this species with nucleic acid ("NA") is believed to only be possible if nucleic acid is present at the time the excited species is generated. Thus, the reaction must, in operational terms, be in the presence of activating wavelengths of electromagnetic radiation, i.e., it is "photobinding"; it is not dark binding. The reaction can be depicted as follows:

C* +NA→NA:C

The product of this reaction is hereinafter referred to as "Photoaddition Product" and is to be distinguished from "Photoproduct."

With this reaction described, one can now consider the situation where nucleic acid is not available for binding at the time the compound is exposed to activating wavelengths of electromagnetic radiation. Since the excited species is short-lived and has no nucleic acid to react with, the excited species may simply return to its ground state:

C*→C

On the other hand, the excited species may react with itself (i.e., a ground state or excited species) to create a ground state complex ("C:C"). The product of these self-reactions where two compounds react is referred to as "photodimer" or simply "dimer." The self-reactions, however, are not limited to two compounds; a variety of multimers may be formed (trimers, etc.).

The excited species is not limited to reacting with itself. It may react with its environment, such as elements of the solvent ("E") (e.g., ions, gases, etc.) to produce other products:

C* +E→E:C

Furthermore, it may simply internally rearrange ("isomerize") to a ground state derivative ("I"):

C*→I

Finally, the excited species may undergo other reactions than described here.

The present invention and the understanding of "photoproduct" does not depend on which one (if any) of these reactions actually occurs. "Photoproduct"—whatever its nature—is deemed to exist if, following the reaction of a compound and activating wavelengths of electromagnetic radiation, there is a resultant product formed that is later capable of binding to nucleic acid in the absence of electromagnetic radiation, i.e., capable of dark binding (whether non-covalent dark binding or covalent dark binding).

It is important to note that, while the definition of "photoproduct" demands that, once formed by exposure to electromagnetic radiation, the product be "capable" of binding to nucleic acid in the absence of electromagnetic radiation, it is not necessary that the product bind only in the dark. Photoproduct may bind under the condition where there is exposure to electromagnetic radiation; it simply does not require the condition for binding. Such a definition allows for both "photobinding" and "photoproduct binding" to nucleic acid to occur at the same time. Such a definition also allows a single compound to be "photoproduct" and "photobinding compound."

In one embodiment, the present invention contemplates dark binding of both psoralen photoproduct and isopsoralen photoproduct to LAR amplification product. With psoralens such as 4'-hydroxymethyl- 4,5',8-trimethylpsoralen (HMT), the present invention contemplates there are a number of resultant products produced when the HMT is exposed to activating wavelngths of electromagnetic radiation. The present invention contemplates that a number of resultant products are similarly produced when isopsoralens such as AMIP and AMDMIP are exposed to activating wavelengths of electromagnetic radiation (particularly when irradiated with the commercially available HRI-100 device). The major resultant products of HMT are two cyclobutyl photodimers. In one of the dimers, the two pyrone rings are linked in a cis-syn configuration, while in the other dimer, the linkage occurs between the furan end of one molecule and the pyrone end of the other, again with cis-syn configuration. A third resultant product of HMT is a monomeric HMT photoisomer. In this isomer, the central ring oxygens assume a 1, 4 instead of the normal 1, 3 orientation. While the two photodimers would not be expected to have an intercalating activity due to geometrical considerations, the photoisomer remains planer, and accordingly, it is contemplated that it has a positive intercalative association with double stranded nucleic acid. Analogously, it is contemplated that some of the resultant products of AMIP and AMDMIP also have a positive intercalative association with nucleic acid. While not limited to any particular theory, non-covalent dark binding is anticipated where monomeric isomers are formed, and particularly, where the positively charge aminomethyl moiety is retained in the structure.

B. Photobinding

The preferred approach of the present invention to binding activation compounds to LAR amplification product is photobinding. Photobinding, as noted above, is defined as the binding of photobinding compounds in the presence of photoactivating wavelengths of light. Photobinding compounds are compounds that bind to nucleic acid in the presence of photoactivating wavelengths of light. The present invention further contemplates the product of photobinding, i.e., a photobinding compound:nucleic acid complex.

IV. Crosslinking

The present invention contemplates a method of sterilization that is useful for, among other uses, solving the carryover problem associated with LAR. The overall approach of the method involves rendering nucleic acid after amplification substantially unamplifiable (hence "Post-Amplification Sterilization"), before a carryover event can occur. The preferred method of sterilization involves crosslinking of nucleic acid with psoralens.

The present invention contemplates introducing psoralens for sterilizing LAR amplification product by A) Random Covalent Addition, B) Site-Specific Covalent Addition, and C) Photoproduct Addition.

A. Random Addition

In one embodiment, the present invention contemplates that crosslinking is preceeded by introduction of psoralen(s) into the reaction mix of a ligase-based amplification protocol. The presence of psoralen(s) does not significantly change the efficiency of amplification. Following amplification, the product is double stranded. Psoralens intercalate among the double stranded product. Upon activation of the amplification products, some of the intercalated psoralen will be driven onto the crosslinks. The crosslinked product will be rendered sterilized since it cannot undergo the strand separation step required for further amplification.

In this embodiment, the present invention contemplates randomly adding psoralen compounds to produce covalently crosslinked LAR amplification product. By random it is not meant that the particular psoralen will not display preferential placement. By random it is meant that the level of addition (one, two or three adducts, etc.) is not limited to one adduct per strand; the compound has access to a larger number of sites.

The present invention further contemplates mixing psoralen compounds to create a "cocktail" for random addition. Randomly added cocktails can be used where multiple adducts per strand are desired and where preferential placement is sought.

Where psoralens are used, consideration should be given to the nature of the LAR amplification product (A:T rich, A:T poor, etc.) in selecting both single mixtures and cocktails for random addition. Where possible, LAR primers should be selected that are A:T rich and which possess many preferred crosslinking sites. These sites are sequences that have adjacent pyrimidines on opposite strands of two complementary LAR primers (e.g., 5'-TpA-3' sequences). Where this is not possible, the present invention contemplates adding AT "tails" to the LAR primer sequence. One example of an appropriate AT "tail" added to the 3' end of a primer is

5'-XXXXXXXXXXXXXXXXXXXXTATATT-3' SEQ ID NO: 10)

where X represents bases in the normal LAR primer sequence (the exact number of bases in the normal sequence is not meant to be indicated).

TABLE 4

POISSON STATISTICS APPLIED TO STERILIZATION
$f_a(n) = [a^n e^{-1}]/n!$
$N = 10^6, f_a(o) = e^{-a}$

| a | $f_a(0)$ | $Nf_a(0)$ |
|---|---|---|
| 3 | 0.050 | $5.0 \times 10^4$ |
| 4 | 0.018 | $1.8 \times 10^4$ |
| 5 | 0.007 | $6.7 \times 10^3$ |
| 6 | 0.0025 | $2.5 \times 10^3$ |
| 7 | 0.0009 | $9.1 \times 10^2$ |
| 8 | 0.0003 | $3.3 \times 10^2$ |
| 9 | 0.00012 | $1.2 \times 10^2$ |
| 10 | 0.000045 | 45.0 |
| 11 | 0.000017 | 17.0 |
| 12 | 0.0000061 | 6.1 |
| 13 | 0.0000023 | 2.2 |
| 14 | 0.00000083 | .8 |
| 15 | 0.00000030 | .3 |
| 16 | 0.00000011 | .1 |
| 17 | 0.00000004 | 0.04 | a = Average number of adducts per strand
$fa_{(0)}$ = Fraction of strands with zero adducts when the average number of adducts per strand is a.
$Nf_a(0)$ = The number of non-sterilized molecules, calculated for a total of $10^6$ molecules (N = $10^6$)

One example of an appropriate AT "tail" added to the 5' end of a primer is

5'-AATATAXXXXXXXXXXXXXXXXX-3' (SEQ ID NO: 11)

where X represents bases in the normal LAR primer sequence (again, the exact number of bases in the normal sequence is not meant to be indicated).

While AT "tails" certainly can help provide sites for crosslinking, the addition of psoralen to nucleic acid is a statistical process. This process can be characterized by measuring an average number (a) of adducts per DNA strand. Not all of the strands will have a adducts per strand. If the addition reaction is governed by Poisson statistics, the fraction of molecules that contain n modifications in a large population of molecules that have an average of a modifications is given by $f_a(n)$ (see Table 4). A fraction of molecules, $f_a(O)$, will contain no modifications and are therefore considered non-sterilized. Table 4 evaluates the non-sterilized fraction of DNA strands that are expected if an average of a modifications per strand exists. Although the fraction of molecules with no modifications is small for all values of a, the expected number of non-sterilized molecules is large when sterilization is applied to a large number of molecules (N). For example, if carryover consisted of $10^6$ product strands, Table 4 shows that $2.5 \times 10^3$ non-sterilized target molecules are expected if there is an average of 6 effective adducts per strand of amplification product.

Alterations of the modification density can be expected through the use of different photoreactive compounds, or the use of the same photoreactive compound at different concentrations. In particular, the modification density is expected to increase through the use of the same photochemical agent at higher concentrations, and attaching the photochemical agent by exposure to actinic light from a device whose optical properties enhance covalent binding.

Increasing the modification density should not interfere with detection of ligase-based amplification products. In this regard, it is not expected that ligase-based amplification products will be detected by hybridization to a probe molecule. Therefore, sterilization compounds can be used in conjunction with ligase-based amplification at higher concentrations.

For a fixed modification density there is another method of improving the sterilization sensitivity limit. The important statistical parameter for sterilization sensitivity is the average number of adducts per strand. By choosing primers judiciously, or by extending the length of the primers at the 5' end or the 3' ends as described previously, the length of the amplification products can be varied, and therefore, the average number of adducts per stand can be varied.

B. Site-Specific Addition

In another embodiment, the present invention contemplates synthetically adding psoralens into one or more primers subsequently used in a ligase-based amplification protocol. Following amplification, the adducted primer (and, therefore, the psoralen) will be incorporated into amplification products. Upon activation of the amplification products, some of the monoadducts will be driven onto the crosslinks if the complementary strand of the amplification product is base-paired with the monoadducted amplification product. This complementary strand can be the full length amplification product or it could consist solely of the complementary primer itself. In either case, the crosslinked product will be rendered sterilized since it cannot undergo the strand separation step required for further amplification.

In this embodiment, the sterilization of amplification product is thus achieved by crosslinking site-specifically-bound psoralen compounds. Site-specifically-bound psoralen compounds avoid the statistical problem of random addition described above and assures that there are adducts on every product.

In one embodiment, the method of the present invention for the construction of specifically placed psoralen adducts begins with the synthesis of thymidine:psoralen monoadduct, followed by the synthesis of thymidine phosphoramidite:psoralen monoadduct, and ends with the incorporation of the monoadduct in the synthesis of LAR primers.

As noted above, LAR utilizes two sets of complementary oligonucleotides for a total of four LAR oligonucleotides or "LAR primers." Each set of LAR primers is complementary to one of the strands of target. The present invention contemplates site-specific addition to one or more LAR primers.

The present invention contemplates a direct chemical method for the preparation of monoadducted LAR primers using phosphoramidite chemistry described in U.S. patent application Ser. No. 225,725, now abandoned, and in the continuing application Ser. No. 07/850,244.

The requisite furan side cis-syn 8Methoxypsoralen (8-MOP):thymidine monoadduct can be prepared and converted to its 5'-dimethoxytrityl-3' -B-cyano-ethoxydiisopropylaminophosphoramidite derivative basically as described by Yabusaki et al., U.S. Pat. No. 4,599,303, hereby incorporated by reference. The yield of 5'-DMT 8-MOP:thymidine monoadduct phosphoramidite, based on starting 8-MOP:thymidine monoadduct, is typically approximately 50%.

DNA synthesis can be conducted using a stepwise automated method such as that employed on an automated DNA synthesizer (Applied Biosystems, Inc.), using a long-chain alkylamine controlled pore glass (CPG) functionalized with the 3'-terminal nucleoside derivative (American Bionetics, Hayward, Calif.) as a solid support. Because of the liability of the 8-MOP:thymidine moiety to strong aqueous base, it is necessary to make modifications to the standard synthesis protocol. The exocyclic amino groups of deoxyadenosine, deoxycytidine and deoxyguanosine should be protected. They can be protected using phenoxyacetyl (PAC) amidites that commerically available from Pharmacia, Inc. Alternatively, they can be protected by 9-fluorenylmethoxycarbonyl (FMOC) groups as described by Webb et al., Nuc. Acids Res. 14, 7661 (1986), and Heikkila et al., Acta Chem. Scand. B37, 263 (1983). The FMOC protected nucleosides are then 5'-dimethoxytritylated and converted to the corresponding 3'—O—cyanoethyl-N,N-diisopropyl (CED) phosphoramidites by standard procedures as described by Beaucage et al., Tetrahedron Letters 22, 1859 (1981). Thymidine CED phosphoramidites can be obtained from American Bionetics or Pharmacia, Inc.. The amidites are used at an approximately thirty-fold molar excess (except the monoadduct phosphoramidite, which is used at approximately fifty-fold molar excess) and activated prior to coupling by "Activator Gold" (Beckman Instruments, Palo Alto, Calif.).

The synthetic cycle consists of detritylation (3% v/v dichloracetic acid in dichloromethane), anhydrous acetonitrile wash, coupling (in the dark in the case of the psoralen containing amidite), anhydrous acetonitrile wash, capping [1:1 mixture of A) 20% v/v 2,6-lutidine, 20% v/v distilled N-methylimidazole in dry THF, and B) 10% v/v acetic anhydride in THF], oxidation (0.5% w/v iodine, 1% v/v 2,6-lutidine, 10% v/v water in THF), and acetonitrile wash.

Following the completion of the synthesis, the CPG is detritylated and washed and the support from each synthesis (ca. 20 mg) is dried in the dark and suspended in 1 ml of 1M 1,8-diazabicyclo[5.4.0]undec- 7-ene (DBU) in acetonitrile for 15 minutes. This removes the FMOC and cyanoethyl protecting groups. The CPG is washed with acetonitrile (3×1 ml) and suspended in concentrated aqueous ammonia for thirty minutes. This removes the deprotected oligomer from the CPG. The ammoniacal solutions are passed over NAP-10 columns (Pharmacia, Uppsalla, Sweden) which are pre-equilibrated with water. The eluants from the NAP-10 columns are taken to dryness in the dark on the Speed-Vac.

The chemical synthesis method offers several advantages over the photochemical procedure reported by Gamper et al., Photochem. Photobio., 40:29 (1984). First, it provides milligram instead of microgram amounts of product. Second, it does not depend on the fortuitous presence of a reactive 5' TpA site in the sequence of interest. Third, it provides a method to prepare long oligonucleotides with site specific monoadducts without a ligation step.

It is not intended that the present invention be limited by the number of adducts incorporated in LAR primers. The present invention contemplates, mono-, di-, tri- and polyadducts. More than one adduct may well be desired, given that driving 100% of monoadducted LAR primers to crosslink is not feasible. Statistically, having more adducts assures that at least one adduct goes on to crosslink and thereby sterilize LAR amplification product. For example, one, two or several monoadducts can be synthetically incorporated into a single primer that is subsequently in an LAR amplification protocol. Following amplification, the adducted primer will be incorporated into amplification products. Upon activation of the amplification products, some of the monoadducts will be driven onto the crosslinks. However, monoadducts that are transiently non-base paired can photoreverse during the activation step and therefore are not capable of participating in the corsslinking event. The use of multiple crosslinking sites in a single primer minimizes the probability that all of the crosslinking sites are lost during the activation process.

The above-described AT "tails" can also be utilized to facilitate site-specific addition. This is particularly true where it is desired that more than one adduct be incorporated in a single LAR primer. In this regard, the present invention contemplates that the careful placement of adducts can enhance sterilization.

Sterilization may be ineffective if two of the LCR primers are capable of hybridizing to a single-strand of ligated product that was previously crosslinked to one of its complementary primers. To avoid this possibility, it is preferred that the multiple monoadducts reside partially on one primer and its complement as just described above and partially on the other two complementary primers of the four primers required for LAR amplification. This latter mode has the advantage that the amplification products will be crosslinked at the two ends of the amplification product. These short products that are covalently linked at both ends are expected to be highly thermally stable and therefore more resistant to further priming reactions.

is specifically due to the interaction of photoproduct with nucleic acid.

Advantages of photoproduct inhibiting methods of the present invention include the ability to preform the inhibition agent in the absence of target. The photoproduct can then be provided at the appropriate point in the process.

V. Design and Use of Self-Sterilizing Primers

The present invention also contemplates sterilization of ligase-based amplification products without the use of sterilizing compounds. In this regard, the present invention contemplates sterilization by use of uniquely designed primers and careful control of temperature during amplification.

In one embodiment, two of the four primers used for amplification have self-hybridizing tails and a non-hybridizing region which together form a "loop" adjacent to the complementary regions of a primer set The important design considerations for the self-hybridizing tails is that the $T_m$ of hybridization (which depends largely on G:C content and length) is such that the loop melts at the temperatures used in the ligase-based amplification process, and yet closes by self-hybridization at temperatures well below the primer annealing step of the amplification process. The important design consideration for non-hybridizing region of the loop is that there is no appreciable impact of the non-hybridizing region on the double strandedness of the self-hybridizing tail region (which depends largely on the size of the non-hybridizing region being greater than seven bases in length).

Figure 2:
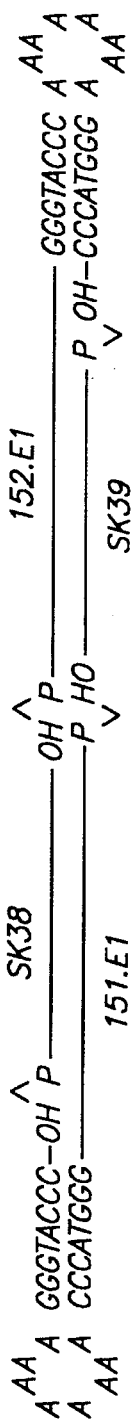
FIG. 2 shows one embodiment of the self-sterilizing primers (SEQ ID NOS: –4) of the present invention.

FIG. 2 shows one embodiment of the self-sterilizing primers of the present invention. The more standard portion of the primers corresponds to HIV sequences. The sequences of these portions are:

SK38 (SEQ ID NO:1) 5'-ATAATCCACCTATCCCAGTAGGAGAAAT

SK39 (SEQ ID NO:4) 5'-TTTGGTCCTTGTCTTATGTCCAGAATGC

151.E1 (SEQ ID NO:3) 5'-ATTTCTCCTACTGGGATAGGTGGATTAT GGGTACCCAAAAAAAAGGGTACCC-3'

152.E1 (SEQ ID NO:2) 5'-GCATTCTGGACATAAGACAAGGACCAAA GGGTACCCAAAAAAAAGGGTACCC-3'

C. Photoproduct Addition

Previous work towards the blocking of replication of nucleic acids with furocoumarins has historically proceeded by a method having the temporal steps: 1) providing a specific psoralen derivative, 2) providing a particular nucleic acid or nucleic acid target sequence(s), 3) mixing the psoralen with the nucleic acid in the presence of activating wavelengths of electromagnetic radiation. In one embodiment, the present invention contemplates a radical departure from this historical approach to blocking. In one embodiment of the method of the present invention, the temporal sequence is the following: 1) providing furocoumarin derivative(s), 2) exposing the furocoumarin derivative (s) to activating wavelengths of electromagnetic radiation, 3) providing a particular nucleic acid or nucleic acid target sequence(s), 4) mixing the irradiated furocoumarin derivative(s) with the nucleic acid. In this embodiment, the furocoumarin is irradiated prior to mixing with nucleic acid. The experimental investigation of this novel temporal sequence has established that furocoumarin photoproduct exists and that photoproduct can inhibit template-dependent enzymatic synthesis, e.g., primer extension.

In one embodiment, the present invention contemplates using HMT photoproduct to sterilize LAR amplification product. While not limited to any particular molecular mechanism for inhibition, it is contemplated that inhibition The loop portion is a poly-A region of eight bases. The self-hybridizing region is a G:C rich region having a predicted $T_m$ of 37° C. in one molar salt.

Figure 3:
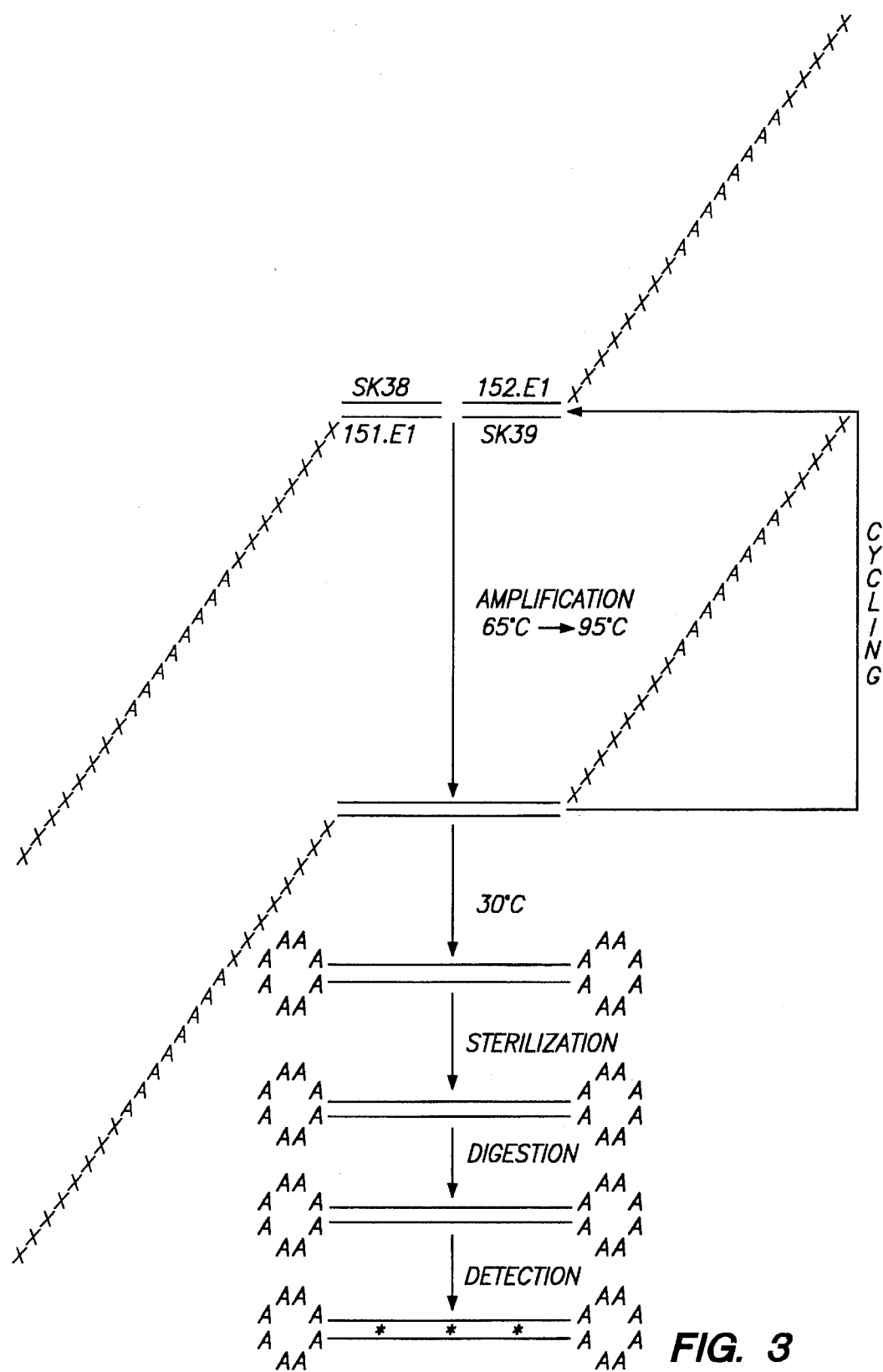
FIG. 3 shows the manner in which sterilization of ligase-based amplification products is carried out using the self-sterilizing primers of the present invention.

FIG. 3 shows the manner in which sterilization above the $T_m$ of the self-hybridizing region) to the is carried out following amplification. The self-sterilizing primers are added (at a temperature well-above the $T_m$ of the self-hybridizing region) to the reation mix (containing, for example, HIV target DNA in a background of genomic DNA, in a volume 10 μl of 20 mM Tris-HCl, pH 7.6/100 mM KCl/10 mM MgCl$_2$/l mM EDTA/10 mM AND$^+$/10 mM dithiothreitol/15 nick-closing units of Taq ligase, overlaid with a drop of mineral oil). The mixture is incubated at 94° C. for 1 minute to create single-stranded template. At this temperature, the self-sterilizing primers will not self-hybridize (i.e., the loop is open). The reaction mixture is then cooled to 65° C., allowing for the hybridization of the self-sterilizing primers to target sequences. Even at this lower temperature, the self-sterilizing primers will not self-hybridize (i.e., the loop remains open).

The mixture can be cycled many times between 65° C. and 95° C. After the desired number of cycles, the reaction mixture is cooled to 30° C. At this lower temperature, the self-sterilizing primers will self-hybridize (i.e., the loop closes). Importantly, the ligase is also active at this temperature and will ligate the self-sterilizing primers to their targets, creating a single-stranded, closed, circular product with a double-stranded region that has a very high $T_m$. This product of the ligation reaction cannot serve as template for subsequent ligation reactions because it will remain largely double-stranded even at 95° C. Hybridization to complementary primers will not occur because self-hybridization is kinetically and thermodernamically more favorable.

There are a number of advantages to this approach. First, no crosslinking compounds are necessary. Second, and most importantly, the self-sterilizing primer system allows for a homogeneous detection method. As shown at the bottom of FIG. 3, amplification and sterilization can be followed with detection by utilizing exonucleases.

For example, Exonuclease III ("Exo") derived from *E. coli*, can be used for this purpose. Exo cleaves bases, one base at a time, from an exposed 3' end of double stranded DNA. Circular DNA does not have an exposed 3' end and is resistent to Exo attack. The amplification products using the self-sterilizing primers, therefore, will not be digested by Exo. By carefully controlling the amount of Exo and the period of treatment, all of the nucleic acid—except the amplification product—can be sufficiently digested to render it undetectable. Since the amplification product remaining is substantially unaffected, it can then be detected easily. In one embodiment, detection is accomplished by adding a fluorescent intercalator, such as ethidium bromide.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); gm (grams); mg (milligrams); µg (micrograms); L (liters); ml (milliliters); µl (microliters); cm (centimeters); mm (millimeters); µm (micrometers); nm (nanometers); ° C. (degrees Centigrade); Ci (Curies); mp (melting point); m/e (ion mass); MW (molecular weight); OD (optical density); EDTA (ethylenediamine-tetracetic acid); 1×TE (buffer: 10 mM Tris/1 mM EDTA, pH 7.5); 1×Taq (buffer: 50 mM KCl, 2.5 mM $MgCl_2$, 10 mM Tris, pH 8.5, 200 µg/ml gelatin); C/M (chloroform/methanol); C/E/T (chloroform/ethanol/triethylamine); C/B/A/F (chloroform/n-butanol/acetone/formic acid); DMF (N,N-dimethylformamide); PAGE (polyacrylamide gel electrophoresis); UV (ultraviolet); V (volts); W (watts); mA (milliamps); bp (base pair); CPM (counts per minute); DPM (disintegrations per minute); TLC (Thin Layer Chromatography); HPLC (High Pressure Liquid Chromatography); FABMS (Fast Atom Bombardment Mass Spectrometry—spectra obtained on a Kratos MS50 instrument—Kratos Analytical, Manchester, England); EIMS (Electron Impact Mass Spectrometry—spectra obtained on an AEI MS-12 Mass Spectrometer—Associated Electric Industries, Manchester, England); NMR (Nuclear Magnetic Resonance; spectra obtained at room temperature on either a 200 MHz or 250 MHz Fourier Transform Spectrometer); Aldrich (Aldrich Chemical Co., Milwaukee, Wis.); Baker (J. T. Baker, Jackson, Tenn.); Beckman (Beckman Instruments, San Ramon, Calif.); BRL (Bethesda Research Laboratories, Gaithersburg, Md.); Cyro (Cyro Industries, Wood Cliff Lake, N.J.); DNEN (Dupont-New England Nuclear, Wilmington, Del. 19805); Gelman (Gelman Sciences, Ann Arbor, MI); Eastman (Eastman Kodak, Rochester, N.Y.); Eastman TLC Plates (#13181 TLC plates with fluorescent indicator, Eastman); EM (EM Science, Cherry Hill, N.J.); Lawrence (Lawrence Berkeley Laboratory, Berkeley, Calif.); Mallinckrodt (Mallinckrodt, St. Louis, Mo.); Pierce (Pierce Chemical Co., Rockford, Ill.); Polycast (Polycast Technology Corp., Stamford, Conn.); Rohm and Haas (Rohm and Hass Co., Los Angeles, Calif.); Sigma (Sigma Chemical Co., St. Louis, Mo.); Spectrum (Spectrum Medical Industries, Los Angeles, Calif.).

To illustrate the advantage of the commercially available HRI-100 irradiation device, a customized light instrument (hereinafter referred to as "the PTI device") was constructed from commerically available parts (at a cost of approximately $10,000.00) to serve as a control. The device is a modified version of a described device. G. D. Cimino et al., Biochemistry 25, 3013 (1986). Some machining was necessary to retrofit some of the commercial parts and to make specialized adapters and holders.

A 500 watt Hg/Xe arc lamp (Model A5000, Photon Technology International) positioned at the focal point of an elliptical mirror in a commercial lamp housing provides the light for the PTI device. The output from the lamp housing passes into an adaptor tube which provides physical support for additional optical accessories and prevents harmful stray UV radiation from emanating into the lab. A mirror deflects the optical beam in the adaptor tube so that it passes through the other optical components.

Two water-cooled, liquid filters are used. These filters have been selected to provide wavelengths of electromagnetic radiation that are appropriate for furocoumarin photochemistry. (Other photoreactive compounds may have wavelength requirements which are quite different from the furocoumarins.) The first filter is fitted with suprasil windows, filled with $H_2O$, and is used to filter out infrared radiation (IR). Exclusion of IR is required to prevent undesired heating of the sample chamber during irradiation, since addition of furocoumarins to nucleic acid is reduced at elevated temperatures. The second liquid filter provides a window of 320–400 nm light for use with furocoumarin photochemical reactions. This particular wavelength window (320–400 nm) excludes both shorter and longer wavelengths which are inappropriate for furocoumarin photochemistry. For example, furocoumarin:nucleic acid complexes undergo photochemical reversal at wavelengths below 313 nm. Exclusion of these wavelengths is necessary for irreversible photobinding of the furocoumarins to occur. This filter (9 cm in length) is fitted with 0.6 cm pyrex windows and filled with an aqueous solution of 0.85% cobaltous nitrate, 2% sodium chloride. An optical diffuser between the the first filter and the second filter provides even illumination over the entire width of the light beam. This diffuser consists of a ground suprasil plate (0.6 cm) fitted into a lens holder.

Light exiting from the first filter passes through an iris so that beam intensity can be controlled. Two lenses focus the beam within the sample holder by first passing the beam through a shutter system, then through the exit of the adaptor tube and finally across a second mirror. The shutter system consists of a rotary solenoid attached to a metal blade which passes between the exit hole of the adaptor tube and a similar hole in a second aluminum plate. This second plate resides adjacent to the exit port of the adaptor tube and also serves as a mount for the solenoid. The power to the solenoid is controlled by a relay which is run off a timer. The sample holder is composed of rectangular brass and can be irradiated either through the side or from the top. It has been machined with passages for the flow of liquids. Thermoregulation of a sample is achieved by connecting this holder to a thermoregulated circulating water bath. The sample holder also contains passages that allow the flow of gasses over the surfaces of the sample vessels (i.e., cuvette faces, etc.) to prevent condensation of water on these surfaces while irradiating at low temperatures. The orifice for the sample vessel in the sample holder is 1 inch by 1 inch by 2.5 inches. A brass adaptor, with slots for the passage of light, permits standard cuvettes to be used, as well as 13 mm test tubes and Eppendorf tubes. The base of the sample holder is hollow so that a bar magnet attached to a small motor can be inserted beneath the sample vessel and function as a magnetic stirrer. Alternatively, the holder can be placed on top of a laboratory stir plate to achieve stirring capabilities. With this irradiation device, the light beam is approximately 0.8 cm diameter at the focal point and it has an intensity of 340 mW/cm$^2$, as measured with a Model J- 221 UV meter (UV Products, San Gabriel, Calif.).

Unless otherwise noted, all sample solutions prepared for irradiation were contained in Eppendorph tubes and irradiated through the sides of the tubes (the HRI-100) or through the top of the tubes (PTI). Eppendorph tubes have a transmittance of only 8 to 5% for wavelengths in the range of 300 nm to 400 nm (data not shown). Therefore, approximately 90% of the actinic light is lost by the use of these sample vessels. Although Eppendorph tubes are the most convenient sample vessels for biochemical and molecular biological procedures, other types of irradiation vessels having better transmission characteristics are comtemplated (e.g., quartz, pyrex, polycarbonate etc.).

Where polyacrylamide gel electrophoresis (PAGE) is used, denaturing (7 or 8M urea) polyacrylamide gels (28 cm×35 cm×0.4 mm) were poured and pre-electrophoresed for 30 to 60 minutes at 2000 Volts, 50 Watts, 25 milliamps. 12% gels were used for oligonucleotides between 40 and 200 base pairs in length; 8% gels were used for longer sequences. Depending on the length of DNA to be analyzed, samples were loaded in either 8M urea, containing 0.025% tracking dyes (bromphenol blue and xylene cyanol), or in 80% formamide, 10% glycerol, 0.025% tracking dyes, then electrophoresed for 2–4 hours at 2000 Volts, 50 Watts, 25 milliamps. Following PAGE, individual bands were, in most cases, visualized by autoradiography. Autoradiography involved exposure overnight at −70° C. to Kodak XAR-5 films with an intensifying screen. In some cases, the visualized bands were cut from the gel and collected for scintillation counting. Scintillation counting involved the use of a scintillation fluid and a commercial scintillation counter (Searle Analytic 92, Model # 000 006893).

Generally, PCR was carried out using 175–200 μM dNTPs (deoxyribonucleoside 5'-triphosphates) and 0.5 to 1.0 μM primers. 5 Units/100 μl of Taqs polymerase was used. PCR reactions were overlaid with 30–100 μl light mineral oil. A typical PCR cycle for HIV amplification using a Perkin-Elmer Cetus DNA Thermal Cycler (Part No. N8010150) was: denaturation at 93° C. for 30 seconds; annealing at 55° C. for 30 seconds; and extension at 72° C. for 1 minute. PCR cycles were normally carried out in this manner for 30 cycles followed by 7 minutes at 72° C.

In many cases, PCR was carried out on an HIV system. This system provides a 115-mer product designated HRI 46 (SEQ ID NO: 12):

5'-ATAATCCACCTATCCCAGTAGGAGAAATTTATAAAAGATGGATAATCCT
GGGATTAAATAAAATAGTAAGAATGTATAGCCCTACCAGCATTCTGGACATAA
GACAAGGACCAAA-3' and its complement, designated HRI 47 (SEQ ID NO: 13):

3'-TATTAGGTGGATAGGGTCATCCTCTTTAAATATTTTCTACCTATTAGGA
CCCTAATTTATTTTATCATTCTTACATATCGGGATGGTCGTAAGACCTGTATT
CTGTTCCTGGTTT-5'.

These sequences were used by C. Y. Ou et al., Science 239:295 (1988).

In many of the examples below, compounds are referred to by their abbreviation (e.g., "HMT" or "AMT"). The formal names for compounds has been described previously.

EXAMPLE 1

Random Addition of Psoralen

It will be desirably in some situations to have precise control of the binding levels of a photoactive compound to nucleic acids for the sterilization of ligase-amplification products. As discussed earlier, photoactive compounds such as psoralen and isopsoralen undergo competing reactions during exposure to actinic light. They will undergo photodecomposition at the same time as they add to polynucleotides. Although the structural properties of a particular photoactive compound determine the relative rates of photodecomposition to photoaddition reactions, the initial concentration of the compound does affect the plateau level of binding.

Figure 4:
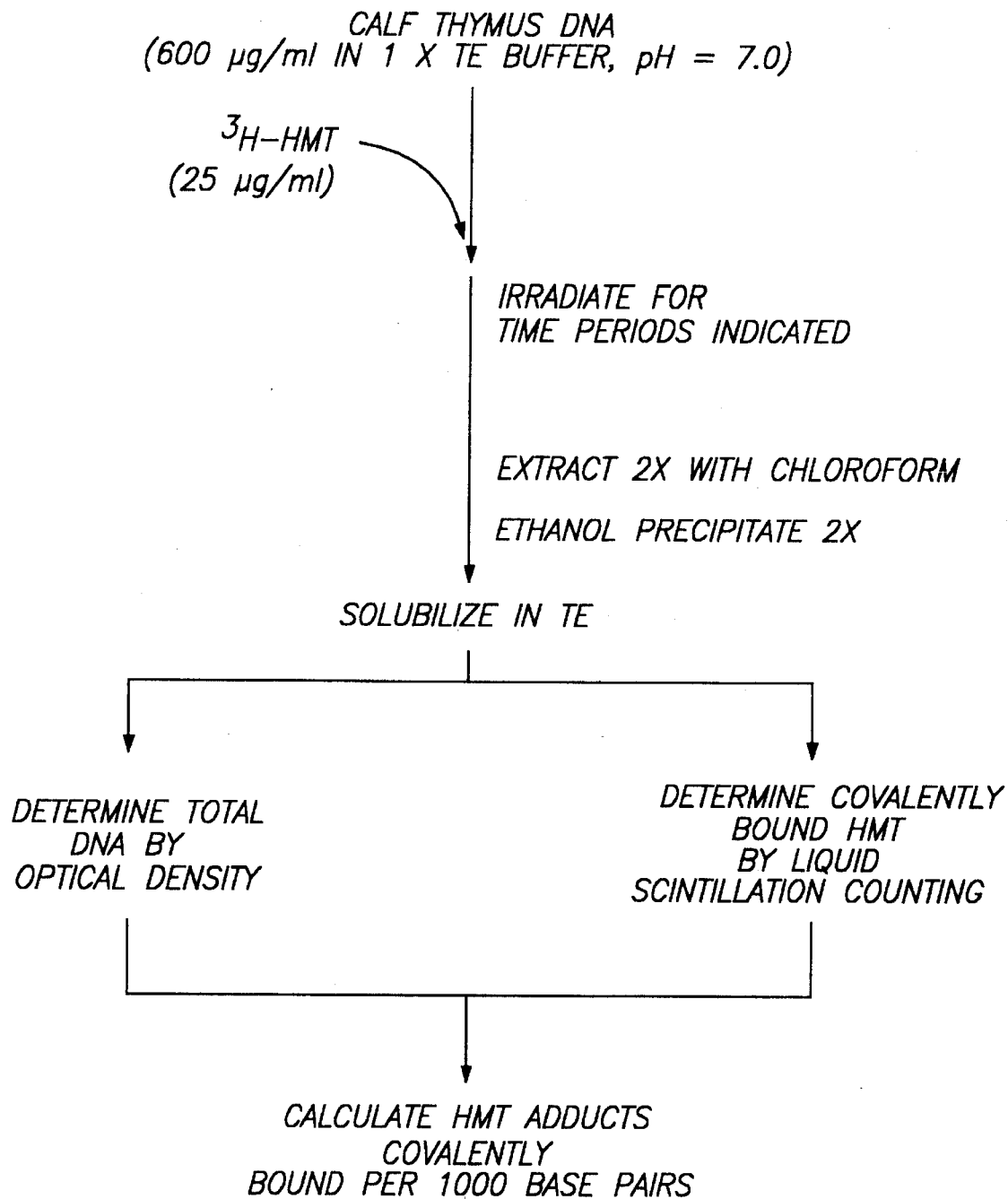
FIG. 4 is a flow chart schematically showing a manner in which random addition of psoralen was measured.

This example investigates the binding levels as a function of irradiation time. Following the procedure outlined in FIG. 4, $^3$H-HMT was used at different concentrations to measure binding to calf thymus DNA. $^3$H-HMT was mixed with the DNA and irradiated using the commercially available HRI-100 irradiation device. The product was then extracted with chloroform to separate the unbound $^3$H-HMT. The nucleic acid was then precipitated and solubilized. Bound HMT was determined by scintillation counting along with measuring the optical density of the DNA solution.

Figure 5:
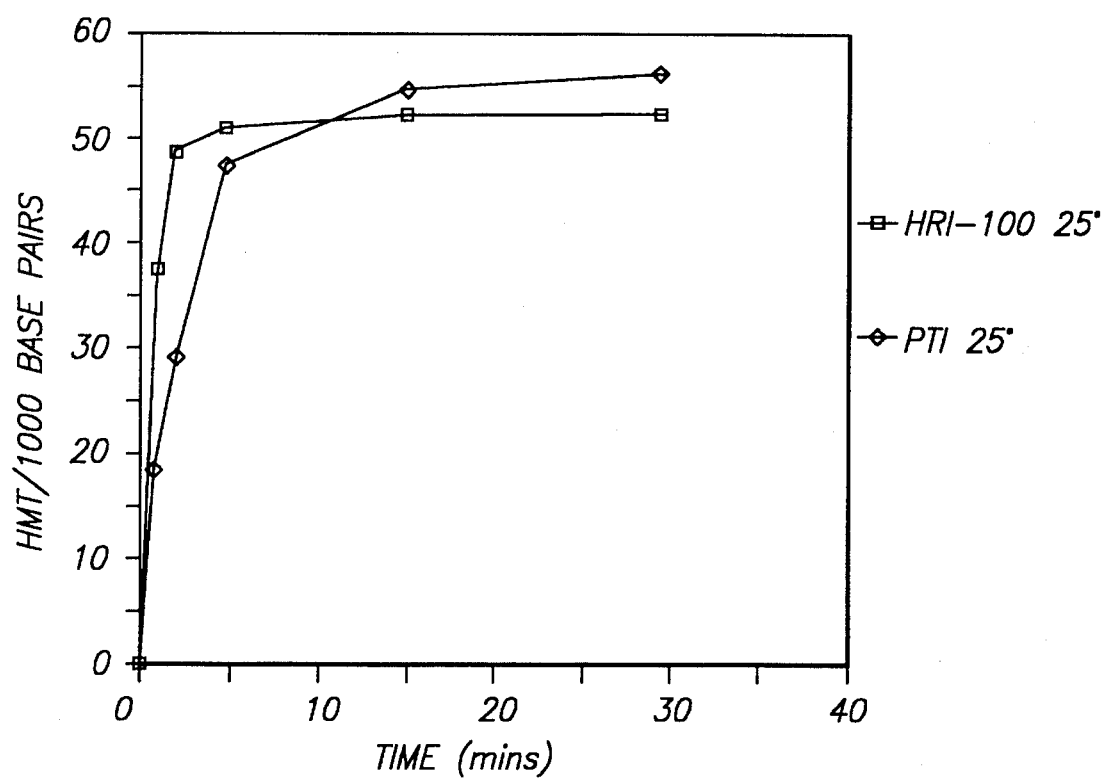
FIG. 5 shows covalent binding of psoralen as a function of time.

The results are shown in FIG. 5. Clearly, binding levels are a function of the irradiation time. Note the advantage of the commercially available HRI-100 device. With this device, providing that the irradiation time is sufficient to achieve the plateau level, a constant level of binding can be achieved.

It should be further noted that, in addition to light exposure, the concentration of the photoactive compound also affects the ultimate binding levels. Providing irradiations are of sufficient duration to achieve plateau levels, the concentration dependence can be used to precisely control addition reactions to a desired level of photobinding.

EXAMPLE 2

Site-Specific Addition of Psoralen

As noted earlier, the present invention contemplates the use of site-specifically added psoralen to primers. Examples of sequences prepared by the chemical synthesis procedure are HRI-69 and HRI-70, which have the following sequences:

| | |
|---|---|
| 5'-*TAG TAA GAA TGT | HRI-69 (SEQ ID NO:14) |
| 5'-AAA *TAG TAA GAA TGT | HRI-70 (SEQ ID NO:15) |
| 3'-TTT AGC ATT CTT ACA | HRI-68 (SEQ ID NO:16) |

As shown, HRI-70 (SEQ ID NO: 15) is a three base extension of HRI-69 (SEQ ID NO: 14). These sequences were selected to demonstrate the ability of an oligonucleotide containing a monoadduct at the 5' end to form crosslink and to show the monoadduct moiety was stable to additional synthetic cycles (i.e., DMT deprotection and oxidation steps). Following synthesis, HRI-69 (SEQ ID NO: 14) and HRI-70 (SEQ ID NO: 15) were characterized as follows. 5' end labelled (32P) HRI-68 (SEQ ID NO: 16) (which is complementary to both HRI-69 (SEQ ID NO: 14) and HRI-70 SEQ ID NO: 15) at $10^{-8}$M was mixed with different concentrations of either monoadducted oligonucleotide ($10^{-8}$ to $10^{-5}$M) under hybridization conditions then irradiated at 320–400 nm for 5 minutes. The samples were analyzed on a denaturing polyacrylamide gel followed by autoradiography. The autoradiogram showed the formation of crosslinks between HRI- 69:HRI-68 (SEQ ID NOS: 14, 16) and HRI-70: HRI-68 (SEQ ID NOS: 15, 16). This result confirmed that the monoadduct phosphoramidite had been incorporated during the synthesis and some fraction of the monoadduct remained structurally intact during the subsequent synthetic steps. Second, each monoadducted oligonucleotide was 3' end labelled with cordycepin and terminal transferase then analyzed on a denaturing polyacrylamide gel. The autoradiogram showed two predominant bands for both HRI-69 (SEQ ID NO: 14) and HRI- 70 (SEQ ID NO: 15) which corresponded to truncated 11-mer plus 12-mer monoadduct (HRI-69SEQ ID NO: 14) and truncated 11-mer plus 15-mer monoadduct (HRI-70SEQ ID NO: 15). The mobility of the bands with respect to the gel standards was as expected. To confirm the identity of the purported monoadduct bands, each was excised and eluted from the gel, mixed with 32P labelled HRI-68, then irradiated as described above. Each monoadduct band produced crosslink with HRI-68 as expected.

EXAMPLE 3

Site-Specific Addition of Psoralen

The sequences that are presented in FIG. 6 describe several oligonucleotides that are used in the synthesis of either a normal 71-mer or the identical 71-mer containing a site-specifically placed psoralen or isopsoralen monoadduct. The 71-mer is a subsequence of the Human Immunodeficiency Virus (HIV) sequence. (An HIV DNA system is described in a application Ser. No. 225,725, now abandoned, and in the continuing application Ser. No. 07/850,244) SK-39 (SEQ ID NO: 4) is a primer oligonucleotide that is complementary to the 3' end of the 71-mers. This primer oligonucleotide can be extended on the 71-mer template to make a complementary strand of the 71-mer.

Figure 7:
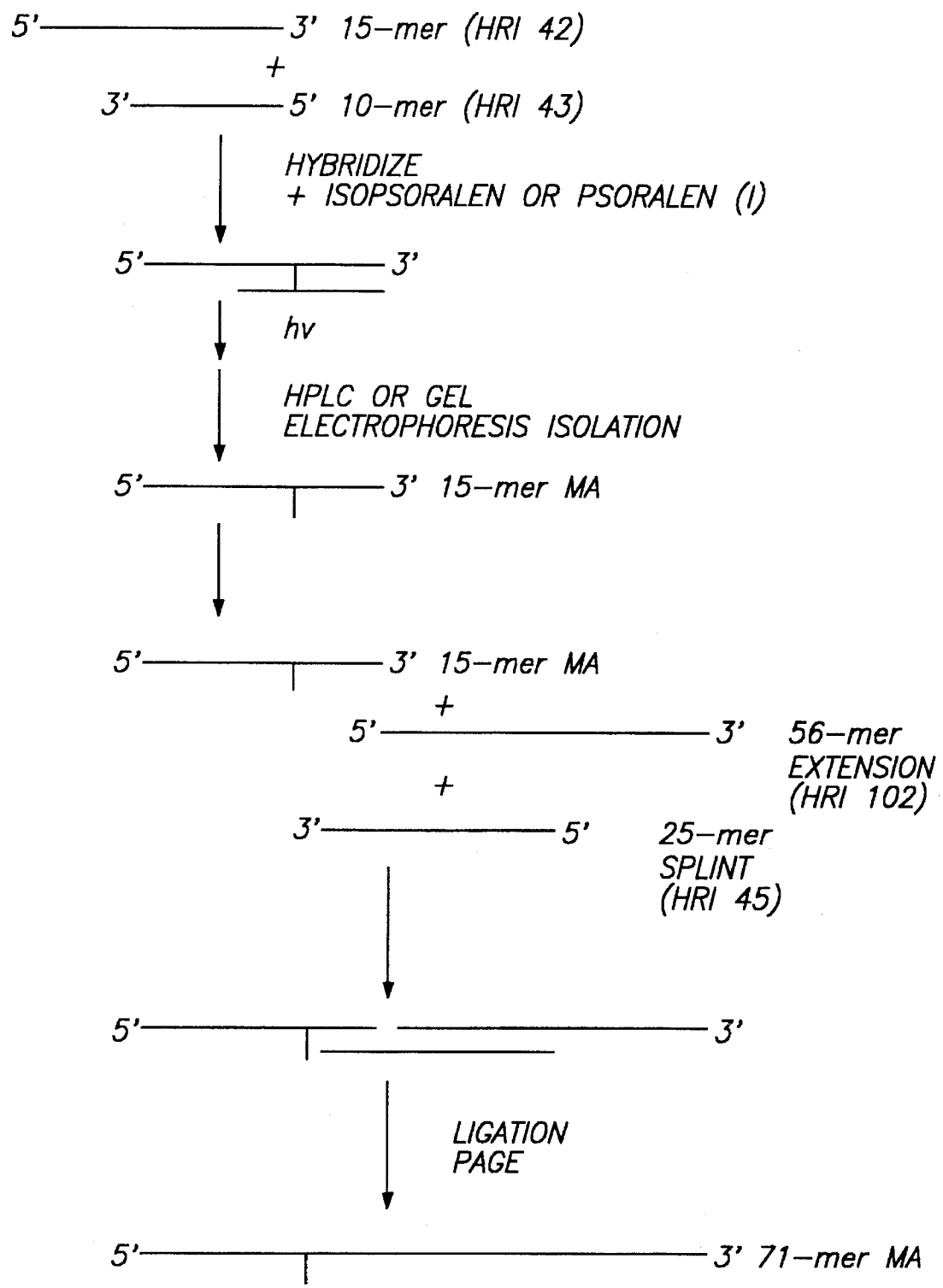
FIG. 7 shows the manner in which site-specific addition was investigated.

FIG. 7 shows the manner in which the site-specific, monoadducted template was derived. In this case, preparation of 71-mers which contain site-specific monoadducts involved 1) preparation of different 15-mer monoadducts from the same unmodified 15-mer (HRI-42 (SEQ ID NO: 10)), and 2) ligation of the different 15-mer monoadducts to the same 56-mer "extender oligonucleotide" (HRI 102 (SEQ ID NO: 8)) using a 25-mer oligonucleotide (HRI-45 (SEQ ID NO: 5)) as a splint. The arrows in FIG. 7 indicate the direction of synthesis, while the monoadduct is indicated by a short line that is perpendicular to the oligomer. While each of the 71-mer monoadducts contains the adduct at a base position that is greater than 56 bases from the 5' end, the precise position of the monoadduct is not meant to be indicated.

To prepare the 15-mer adducts, the 15-mer was incubated with a complementary 10-mer along with psoralen or isopsoralen under hybridization conditions. The mixture was then irradiated to provide the monoadducted 15-mer. While the invention is not dependent on knowing the precise mechanism of coupling, it has generally been believed that the 10-mer directs the isopsoralen or psoralen to a single TpA site within the double-stranded helix formed by the 10-mer/15-mer hybrid. After isolation of an HPLC peak believed to contain the 15-mer with a single psoralen or isopsoralen monoadduct, these 15-mer monoadducts were ligated to a 56-mer extender in order to provide the monoadducted 71-mers for use as polymerase templates. The ligation reaction therefore utilized three oligonucleotides: the particular psoralen or isopsoralen monoadducted 15-mer, the 56-mer extender, and the 25-mer splint. The ligation complex was hybridized together then ligated. The ligated product was then isolated as a single band by denaturing PAGE.

To provide highly purified 71-mers which contain a single monoadduct, it was necessary to provide highly purified 15-mer monoadduct prior to the ligation step. This was accomplished by repurification of the HPLC purified monoadducted 15-mers by PAGE. In this way, essentially all the non-monoadducted 15-mer was removed prior to ligation. Separation of 15-mer monoadduct from unmodified 15-mer was readily accomplished by PAGE (while the same technique is not effective for separation of the corresponding unmodified 71-mer and monoadducted 71-mer sequences). In this manner, exceedingly pure monoadducted 71-mers were produced for the primer extension reactions; monoadducted 71-mers (as well as unmodified 71-mers) are used in Example 3, below.

EXAMPLE 4

Rendering Nucleic Acid Unamplifiable

This example demonstrates the ability of site-specifically added psoralens to render nucleic acid unamplifiable. This experiment examines the ability of HMT to block Taq polymerase on an HIV template.

Figure 8:
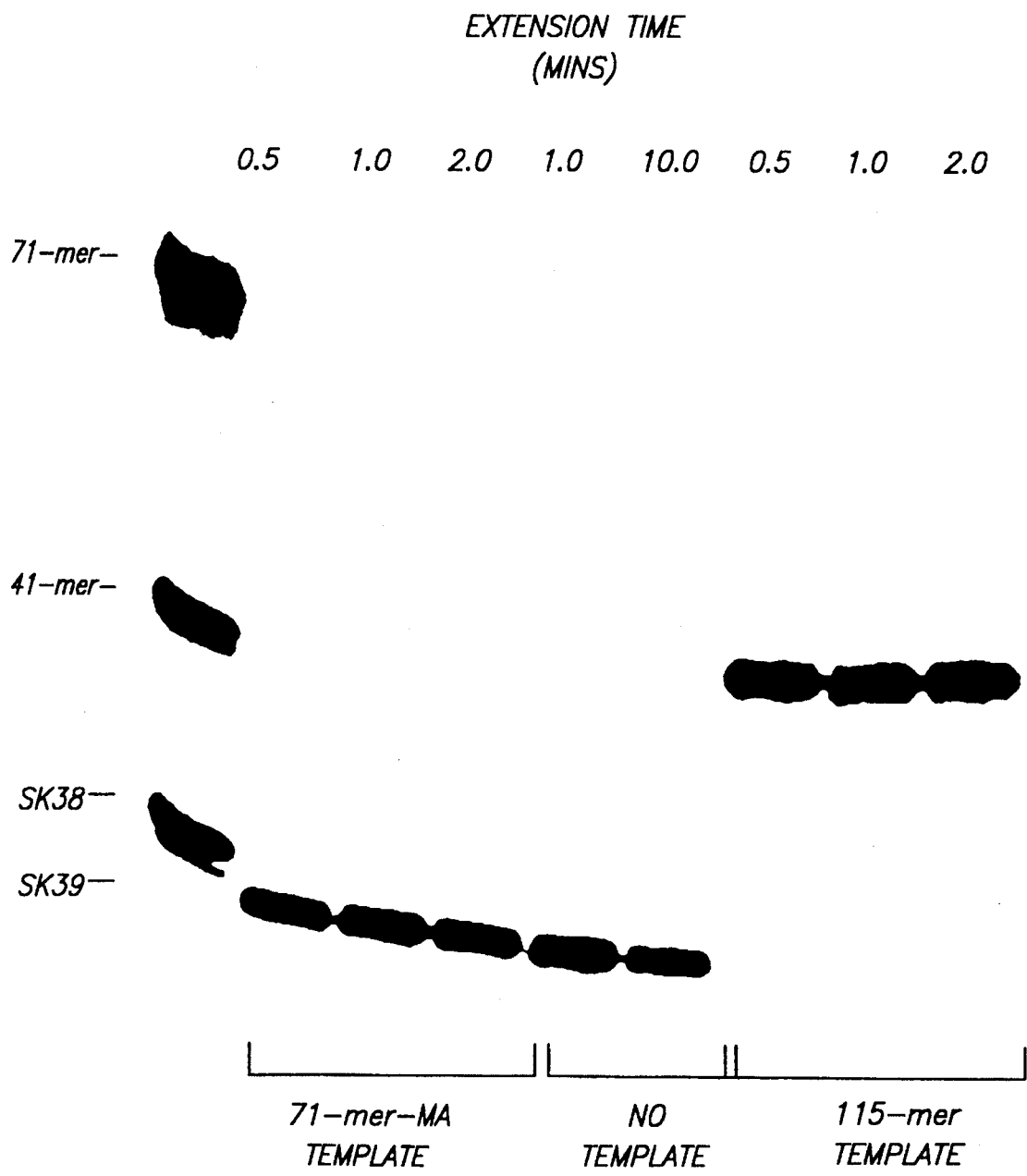
FIG. 8 shows results with a site-specifically added HMT monoadduct.

Monoadducted 71-mer was constructed as described in FIG. 7, but for HMT. Extension was carried out and analyzed as before on PAGE. The results for Taq polymerase are shown in FIG. 8. Clearly, HMT monoadducts stop Taq polymerase. Full length 71-mer is not made and a shorter strand corresponding to the position of the HMT adduct was made.

EXAMPLE 5

Non-Psoralen Activation Compounds

The above examples show embodiments of the present invention utilizing psoralen compounds. In this experiment, the ability of two different Phenylazide derivatives (see Table 1), photobiotin (Vector Labs) and monoazide ethidium chloride, to block replication of 71-mer was investigated by randomly adding each compound to the 71-mer. Again, addition may only be random in the sense that one or more adducts may be formed with any one strand of nucleic acid.

The actual placement of these compounds may be governed by preferential binding at particular sites (e.g., A:T). In addition to blockage by random adducts, there may be inhibition by photoproducts.

The two compounds, photobiotin and monoazide ethidium chloride, have different spectral characteristics. To activate these compounds, two different wavelength regions were selected using a single light source (General Electric Sunlamp, Model RSM, 275 watt). The light source was positioned 10 cm above uncapped Eppendorf tubes which contained samples to be irradiated. The samples were kept on ice during irradiation. A pyrex dish was placed between the lamp and the samples:

For samples containing photobiotin, 2.5 cm of water was added to the pyrex dish to help remove some of the infrared radiation. The samples were irradiated for 15 minutes.

For samples containing monoazide ethidium chloride, wavelengths less than 400 nm were filtered out by using 2.5 cm of an aqueous solution of 2.9M $NaNO_2$. Removal of short wavelengths (i.e., wavelengths shorter than 400 nm) is necessary for the use of monoazide ethidium chloride. Irradiation of this compound with shorter wavelengths results in conversion to non-active forms (data not shown). Wavelengths below 400 nm are therefore undesirable for use with this compound.

In this experiment, the 71-mer template ($2\times10^{-9}$ M) in 10 μl was mixed with either no photoreactive compound, photobiotin ($6\times10^{-6}$M), or monoazide ethidium ($1.4\times10^{-3}$M). Half of each of these samples were irradiated on ice for 15 minutes with wavelengths appropriate for each specific photoreactive compound. The other half of the samples were kept in the dark as controls. The samples containing no photoreactive compound were exposed with the water filter in place. $^{32}$P-SK-39 primer ($1\times10^{-8}$M), dNTPs (200 μM), and additional buffer were added to yield a volume of 18 μl. The samples were then denatured at 95° C. for 5 minutes, and then equilibrated at 55° C. for 3 minutes. Taq polymerase was then added and extension was allowed to proceed for 5 minutes at 55° C. The reactions were stopped by bringing the samples 10 mM in EDTA. The products were examined by PAGE (data not shown). The controls containing no photoreactive compound, no photoreactive compound plus light, and photobiotin (Dark control) all showed similar amounts of full length extension product. No truncated products were observed with these samples. The dark control with monoazide ethidium chloride resulted in inhibition of extension. Photobiotin, by contrast, showed inhibition only after irradiation.

EXAMPLE 6

Photoproduct

The non-psoralen compounds, photobiotin and monoazide ethidium chloride, examined above are now tested to measure photoproduct; the temporal steps were performed to examine photoproduct effects (if any).

Solutions of photobiotin and monoazide ethidium chloride were made up in 1×Taq buffer. Concentrations of photobiotin ranged form $7\times10^{-4}$M to $7\times10^{-10}$M: concentrations of the monoazide ethidium chloride ranged from $3\times10^{-6}$M to $3\times10^{-10}$ M. The high-end of these concentration series was based on earlier experiments that showed that higher concentrations of these compounds shut down PCR by dark binding. Each compound solution was divided into two parts: One part was irradiated under a GE sunlamp through a pyrex filter (300 nm cut-off); the other half was irradiated under a GE sunlamp through a 2.9M $NaNO_2$ liquid filter (400 nm cut-off). Irradiations were carried out on ice for 15 minutes. After irradiation, aliquots of each tube were carried over into tubes containing PCR reagents and target (HIV 115-mer); PCR was then carried out for 30 cycles in the presence of $\alpha$-$^{32}$P-dCTP. After amplification aliquots were analyzed on 12% acrylamide/8M urea gels (data not shown).

The results obtained show that monoazide ethidium chloride, when tested in this mode, does not inhibit PCR; 115-mer amplified at the high concentration points. By contrast, when used in this mode, photobiotin shut down PCR at the highest concentration used ($7\times10^{-4}$M) (115-mer amplified at all lower concentrations).

Given these results, it is believed that blocking of primer extension seen above with the monoazide ethidium chloride was probably due to photobinding and not photoproduct binding. The results seen here with photobiotin, however, suggest that the previous blocking was probably due to photobiotin photoproduct.

EXAMPLE 7

Sterilization Using AMT

In this example, sample template is prepared for liagebased amplification. AMT is added prior to amplification at a concentration of 100 μg/ml. Instead of primer pair SK-38/39 (SEQ ID NOS: 1, 4), the biotinylated analogs, in which biotin has been appended to the 5' end of one or both primers via an intervening tetraethylenglycol bridge (ester linkage to the biotin), are used. Following 30 cycles of amplification, the reaction vessel is exposed to 300–400 nm light on the HRI-100 device. Following irradiation, the reaction vessel is opened and the product removed. Free primer is then removed by spinning the PCR reaction mix through a Centricon 100 (Amicon Division, W R Grace & Co., Danvers, Mass.). The Centricon filters consist of a semipermeable membrane which permits the passage of short oligonucleotides, but not long oligonucleotides. Amplification product is differentially retained in the retentate. Several washes are required (these membranes are conveniently mounted in a disposable plastic tube that is spun in a centrifuge for 5 mins at 2000×g). After the final wash, the retentate is immobilized on a nylon membrane or a nitrocellulose membrane by filtration. The filter is then baked under vacuum for 2 hours at 80° C. After immobilization, the amplification product is detected with a commercially available biotin detection systems (BluGene Detection System; catalog #8179 SA; BRL).

EXAMPLE 8

Dark Binding of Non-Psoralen Compounds

This example investigated the concentrations at which non-psoralen compounds inhibited amplification in the absence of light. The compounds tested were the following: 1) ethidium bromide (a Phenanthridine, see Table 1), 2) xylene cylanol (an Organic Dye, see Table 1), 3) bromphenol blue (an Organic Dye, see Table 1), 4) coumarin and 5) methylene blue (a Phenazathionium Salt, see Table 1).

The first dark control was run with compounds 1–3. All the compounds showed some inhibition of amplification at the higher concentrations used (data not shown).

A separate experiment examined inhibition with coumarin and methylene blue in the absence of light. The following concentrations of methylene blue were tried: $4.3 \times 10^{-2}$, $4.3 \times 10^{-3}$, $4.3 \times 10^{-4}$ and $4.3 \times 10^{-5}$M. Concentrations of coumarin tried included: $7 \times 10^{-3}$, $7 \times 10^{-4}$, $7 \times 10^{-5}$ and $7 \times 10^{-6}$M. Compound was added to the reaction tube containing $\alpha$-$^{32}$P-dCTP and target. Amplification was carried out for 30×cycles. Samples were loaded onto a 12%/8M urea gel. The results (not shown) indicate that methylene blue inhibited amplification at concentrations above $4.3 \times 10^{-5}$M. Coumarin did not inhibit amplification at any of the concentrations tested.

EXAMPLE 9

Solvents

The impact of a given concentration of sterilizing compound on ligase-based amplification efficiency must be determined on a system by system basis. For example, the HIV 115-mer system is compatible with concentrations of sterilizing compound up to 400 μg/ml, and therefore this concentration may be used for sterilization. However, this concentration may not be compatible with other target systems. Indeed, the amplification efficiency of some target systems may be compromised by high concentrations of sterilizing compounds.

High concentrations of sterilizing compounds may function to stabilize the amplification product (particularly long products or products which are exceptionally GC rich) such that less of the double stranded product will denature each cycle. This reduced availability of single stranded product for subsequent priming and extension would reduce the product yield in each LAR cycle. This reduced efficiency over many LAR cycles would result in drastic reduction in the yield of amplification product.

One method to overcome stabilization of amplification product is to modify the amplification conditions such that the melting temperature of the amplification product is lowered. In so doing, more of the double stranded product is denatured each cycle thereby providing more single stranded target for subsequent priming and ligation. The net result of the modified conditions is a higher yield of product.

One modification of amplification conditions which provides more denatured (single stranded) product is to raise the pre-set denaturation temperature above 95° C. for each cycle. This modification has the disadvantage of concomitant inactivation of ligase at temperatures above 95° C. Another modification is adding a co-solvent to the amplification buffer which allows denaturation of the product to occur at a lower temperature. Such cosolvent are dimethyl sulfoxide (DMSO) and glycerol. In this example, the effect of DMSO on amplification in the presence of high concentrations of sterilizing compound is investigated.

Samples are prepared for LAR which contain 1 μg of human placental DNA either with or without (unirradiated) AMT (200 μg/ml). The samples are amplified 30 cycles under standard LAR conditions in the presence of 0%, 1%, 5% or 10% DMSO. Following amplification, the samples are analyzed. The results indicate that addition of DMSO as a co-solvent allows amplification to proceed in the presence of AMT.

Although the foregoing invention has been described in some detail by way of illustration and example for purposes of clarity and understanding, it will be readily apparent to those of ordinary skill in the art in light of the teaching of this invention that certain changes and modifications may be made thereto without departing from the spirit or scope of the appended claims.

We claim:

1. A method for rendering ligase-based amplification product unamplifiable, comprising the sequential steps:

a) providing in any order, i) at least two primers each of said primers comprising a self-hybridizing region of at least four bases, said region having a $T_m$ such that self-hybridization occurs at a temperature below that used for amplification, and a non self-hybridizing region of greater than seven bases, and ii) sample template,
iii) amplification reagents,
iv) at least one enzyme having ligase activity, and
v) means for containing a reaction;

b) adding to said reaction containing means, in any order, said primers, said sample template, said amplification reagents, to make a reaction mixture;

c) adding said enzyme having ligase activity to said reaction mixture, at a temperature above said $T_m$ of said self-hybridizing region of said primers, to create a ligase-based amplification product; and d) cooling said reaction mixture to a temperature at or below said $T_m$ of said self-hybridizing region of said primers, so that said self-hybridizing region of said primers self-hybridizes to form a loop in said non self-hybridizable region of said primers, under conditions such that said enzyme having ligase activity creates a circular amplification product that is unamplifiable in any subsequent amplification reaction having conditions similar to those used in step c) above.

2. The method of claim 1 further comprising, immediately after said adding of said enzyme having ligase activity, the step of closing said reaction containing means.

3. The method of claim 2 wherein said reaction containing vessel is maintained in a closed condition until the completion of step d).

4. The method of claim 1 further comprising, after step d), the step of detecting said unamplifiable, ligase-based amplification products.

5. The method of claim 4 wherein said detecting comprises the sequential steps of i) enzymatically digesting all nucleic acid in said reaction mixture except said unamplifiable, ligase-based amplification products, and ii) adding a reporter molecule to said reaction mixture.

6. The method of claim 5 wherein said enzymatic digestion is performed using Exonuclease III.

7. The method of claim 5 wherein said reporter molecule comprises a fluorescent intercalator.

8. The method of claim 7 wherein said fluorescent intercalator is ethidium bromide.

9. The method of claim 1, wherein each of said self-hybridizing regions consists of eight bases.

10. The method of claim 1, wherein said self-hybridizing region is G:C rich.

11. The method of claim 1, wherein each of said non self-hybridizing region consists of eight bases.

12. The method of claim 1, wherein four of said primers are employed, two of said primers are non self-hybridizing, each primer having termini which will bind to target nucleic acid sufficiently adjacent so as to permit amplification to occur in step c).

13. A method for rendering ligase-based amplification product unamplifiable, comprising the sequential steps:

a) providing in any order,
   i) at least four primers, at least two of said primers comprising a self-hybridizing region of eight bases or more, said self-hybridizing region having a $T_m$ such that self-hybridization occurs at a temperature below that used for amplification, and a non self-hybridizing region of greater than seven bases, at least two of said primers comprising non self-hybridizing primers,
   ii) sample template,
   iii) amplification reagents,
   iv) at least one enzyme having ligase activity, and
   v) means for containing a reaction;

b) adding to said reaction containing means, in any order said primers, said sample template, said amplification reagents, to make a reaction mixture;

c) adding said enzyme having ligase activity to said reaction mixture, at a temperature above said $T_m$ of said self-hybridizing region of said primers, to create a ligase-based amplification product;

d) cooling said reaction mixture to a temperature at or below said $T_m$ of said self-hybridizing region of said primer, so that said self-hybridizing region of said primers self-hybridizes to form a loop in said non self-hybridizing region of said primers under conditions such that said enzyme having ligase activity creates a circular amplification product that is unamplifiable in any subsequent amplification reaction having conditions similar to those used in step c) above; and e) detecting said unamplifiable ligase-based amplification products by
   i) enzymatically digesting all nucleic acid in said reaction mixture except said unamplifiable, ligase-based amplification products, and
   ii) adding a reporter molecule to said reaction mixture.

14. The method of claim 13, wherein said enzymatic digestion is performed using Exonuclease III.

15. The method of claim 13, wherein said reporter molecule comprises a fluorescent intercalator.

16. The method of claim 15, wherein said fluorescent intercalator is ethidium bromide.

* * * * *